United States Patent
Gstrein et al.

(10) Patent No.: US 8,148,484 B2
(45) Date of Patent: Apr. 3, 2012

(54) BIOCIDAL POLYMERS

(75) Inventors: Xaver Norbert Gstrein, Gloggnitz (AT); Wolfgang Kern, Seiersberg (AT); Karl Rametsteiner, Linz (AT); Gerhard Seyfriedsberger, Timelkam (AT); Franz Stelzer, Graz (AT)

(73) Assignee: KE Kelit Kunststoffwerk GesmbH (AT)

( * ) Notice: Subject to any disclaimer, the term of this patent is extended or adjusted under 35 U.S.C. 154(b) by 808 days.

(21) Appl. No.: 12/090,568

(22) PCT Filed: Oct. 16, 2006

(86) PCT No.: PCT/EP2006/067452
§ 371 (c)(1),
(2), (4) Date: Jun. 2, 2008

(87) PCT Pub. No.: WO2007/045634
PCT Pub. Date: Apr. 26, 2007

(65) Prior Publication Data
US 2008/0251460 A1 Oct. 16, 2008

(30) Foreign Application Priority Data

Oct. 17, 2005 (AT) ................. A 1692/2005

(51) Int. Cl.
*C08G 61/08* (2006.01)
*C08L 65/00* (2006.01)
*A61K 31/33* (2006.01)

(52) U.S. Cl. ........ 526/282; 526/257; 526/260; 526/265; 526/268; 526/274; 526/279; 526/281; 525/103; 525/123; 525/175; 525/182; 525/203; 525/204; 525/206; 525/209; 525/210; 424/78.32

(58) Field of Classification Search .................. 526/274, 526/281, 257, 260, 265, 268, 279, 282; 525/103, 525/123, 175, 182, 203, 204, 206, 209, 210; 424/78.32
See application file for complete search history.

(56) References Cited

U.S. PATENT DOCUMENTS

| 4,176,220 | A | * | 11/1979 | Ikeda et al. ................. 526/97 |
| 4,532,269 | A | | 7/1985 | Gitlitz et al. |
| 4,812,543 | A | * | 3/1989 | Matlack et al. ............. 526/281 |
| 4,883,851 | A | * | 11/1989 | Grubbs et al. ............. 526/268 |
| 6,790,910 | B1 | | 9/2004 | Sosna et al. |
| 2006/0115448 | A1 | * | 6/2006 | Tew et al. ................. 424/78.3 |

FOREIGN PATENT DOCUMENTS
WO WO 01/18077 3/2001

OTHER PUBLICATIONS

International Search Report dated Apr. 19, 2007 issued in corresponding PCT Application No. PCT/EP2006/067452.
*Tuning the Hemolytic and Antibacterial Activities of Amphiphilic Polynorbornene Derivatives*; M. Firat Ilker, Klaus Nusslein, Gregory N. Tew and E. Bryan Coughlin; J. Am. Chem. Soc. 2004, 126, 15870-15875.
*Synthesis of Norbornenyl Polymers with Bioactive Oligopeptides by Ring-Opening Metathesis Polymerization*; Heather D. Maynard, Sheldon Y. Okada and Robert H. Grubbs; Macromolecules 2000, 33, 6239-6248.
*Modular Norbornene Derivatives for the Preparation of Well-Defined Amphiphilic Polymers: Study of the Lipid Membrane Disruption Activities*; Firat Ilker, Hanna Schule and E. Bryan Coughlin; Macromolecules 2004, 37, 694-700.
English translation of International Preliminary Report on Patentability dated Mar. 7, 2008.

* cited by examiner

*Primary Examiner* — Fred M Teskin
(74) *Attorney, Agent, or Firm* — Ostrolenk Faber LLP

(57) ABSTRACT

Norbornene-based biocidal polymers having primary, secondary or tertiary amine or phosphine end groups, the parent monomers, processes for preparing the monomers and polymers, and their use.

7 Claims, No Drawings

BIOCIDAL POLYMERS

CROSS REFERENCE TO RELATED APPLICATIONS

The present application is a 35 U.S.C. §371 National Phase conversion of PCT/EP2006/067452 filed Oct. 16, 2006, which claims priority of Austrian Application No. A1692/2005 filed Oct. 17, 2005. The PCT International Application was published in the German language.

TECHNICAL FIELD

The invention relates to biocidal polymers which are based on monounsaturated bicyclic or quadricyclic monomers having nitrogen functionalities or phosphorus functionalities, to processes for preparing them, and to their use.

BACKGROUND OF THE INVENTION

There are a multiplicity of microorganisms which colonize on surfaces and propagate to form biofilms. Such colonization may be unwanted for a large number of reasons, such as, for example, hygiene concerns in the case of medical articles or transport materials and packaging materials for foodstuffs and comestibles, or economic considerations in the case of boat hulls.

One way of avoiding colonization by microorganisms is the regular treatment of at-risk surfaces with disinfectants for external application. Disadvantages of a procedure of this kind include the need for frequent repetition of the treatment, the difficulty of estimating the amounts required, and the often unhealthy qualities of the disinfectants.

Another way of avoiding colonization by microorganisms is to use materials whose surfaces are biocidally active. Such materials can be produced, for instance, by incorporating biocidally active substances into a base material. Organometallic compounds, metal salts of tin, silver or copper, for example, or specific organic compounds are known to act as biocides. When such compounds are admixed to a plastic or to a surface coating, a decay-inhibiting or biocidal activity is obtained. According to U.S. Pat. No. 4,532,269, for example, a terpolymer of butyl methacrylate, tributyltin methacrylate, and tert-butylaminoethyl methacrylate can be used as an antimicrobial marine coating. Disadvantages of such materials reside in the decrease in their biocidal activity over time, since the concentration of the biocidal substances in the base material disappears continuously through diffusion and leaching, and in the environmental pollution associated with this release of the biocidal substances.

Moreover, polymer materials having biocidal properties can be obtained by using monomers substituted with biocidally active groups to produce said materials. In this case the biocidal activity is long-lasting and is not reduced by gradual leaching and diffusion.

Accordingly, EP0862858 describes a copolymer of tert-butylaminoethyl methacrylate and aliphatically unsaturated monomers. WO0118077 discloses a homopolymer of acryloyloxy-alkylamines or methacryloyloxyalkylamines.

Ilker et al., Macromolecules 2004, 37, 694-700, disclose antibacterial polymers of cyclic anhydrides or imides based on norbornene.

SUMMARY OF THE INVENTION

It is an object of the present invention to develop further biocidally active polymers whose presence leads to the destruction of microorganisms and which prevent colonization of microorganisms on surfaces.

Unexpectedly it has been found that, by polymerization of certain norbornene derivatives, polymers having excellent biocidal activity can be obtained.

The application accordingly provides biocidal polymers comprising structural repeating units according to at least one of the formulae 1 and 2

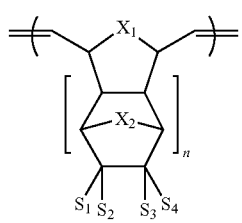

formula 1

$n = 0, 1$

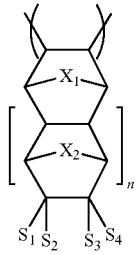

formula 2

$n = 0, 1$ where X1 and X2 can be identical or different and where X1 and X2 can be
—$CH_2$—, —$CH_2$—$CH_2$—, —O—, —S—, —N(R1)-, —P(R1)-, =(C=C(R2)R3),
with R1, R2, R3=H, straight-chain or branched $C_1$-$C_{20}$ alkyl, where R2 and R3 can be identical or different,
and where the substituents S1, S2, S3, S4 can be identical or different
where S1, S2, S3, S4=H, straight-chain or branched $C_1$-$C_{20}$ alkyl, cycloalkyl, aralkyl, alkylaryl, aryl, -a-d, -a-b-d, -b-c-d, -a-b-c-d,
where at least one of the substituents S1, S2, S3, S4 is a-d, -a-b-d, -b-c-d, -a-b-c-d,
and where a can be a straight-chain or branched $C_2$-$C_{20}$ alkylene, preferably $C_2$-$C_6$ alkylene which optionally is substituted one or more times by one or more halogen groups,
or a siloxane, an oligo- or poly-siloxane having 1-20 repeating units,
or oxymethylene or a polyoxymethylene —(O—$CH_2$)$_k$— where k=1-20,
or a $C_2$-$C_4$ alkylene glycol or $C_2$-$C_4$ polyalkylene glycol having 1-20 repeating units,
or a cycloalkylene,
or an aralkylene,
or an alkylarylene,
or an arylene,
or an alkylenearylene,
or an arylenealkylene,
and where b can be —O—, —O—CO—, —CO—O—, —O—CO—O—, —CO—, —CO—NH—, —NH—CO—, —S—, —$SO_2$—, —SO—, —O—CS—O—, —N(R6)- where R6=H, straight-chain or branched $C_1$-$C_6$ alkyl, aryl, aralkyl, alkylaryl, —O—CO—NH—, —NH—CO—NH—, —O—CS—NH—, —NH—CS—NH—, —NH—C(NH)—NH, —NH—CO—O—, —NH—CS—O—,
and where c can be a straight-chain or branched $C_1$-$C_{20}$ alkylene, preferably $C_1$-$C_6$ alkylene, which optionally is substituted one or more times by one or more halogen groups,
  or a siloxane, an oligo- or poly-siloxane having 1-20 repeating units,
  or oxymethylene or a polyoxymethylene —(O—$CH_2$)$_k$— where k=1-20,
  or a $C_2$-$C_4$ alkylene glycol or $C_2$-$C_4$ polyalkylene glycol having 1-20 repeating units
  or a cycloalkylene,
  or an aralkylene,
  or an alkylarylene,
  or an arylene,
  or an alkylenearylene,
  or an arylenealkylene,
and where d can be
  -e(R4)R5 where e=N or P,
  where the group -e(R4)R5 can be a guanidinyl radical —NH—C(NH)—$NH_2$, an N-substituted gyanidinyl radical, a biguanidinyl radical, a hydrazinyl radical —NH—$NH_2$ or an N-substituted hydrazinyl radical,
  and where, in the group -e(R4)R5,
    the radicals R4 and R5 can be identical or different where R4, R5=H, straight-chain or branched $C_1$-$C_{20}$ alkyl, aralkyl, alkylaryl, aryl, cycloalkyl, heteroaryl,
  or the radicals R4 and R5
    together with N of the group —N(R4)R5 can form an azirine, aziridine, azete, dihydroazete, azetidine, pyrrole, pyridine, azepine or azapan ring, where the nitrogen of the group —N(R4)R5 in such unsaturated rings may optionally form a double bond to one of the substituents R4, R5 and may therefore be in quaternized form in the group —N(R4)R5,
    or together with N of the group —N(R4)R5 and with one or more further unsubstituted or substituted heteroatoms from the group —O—, —S—, —NH—, —N(R7)-
    where R7=H, straight-chain or branched $C_1$-$C_{20}$ alkyl, aralkyl, alkylaryl, cycloalkyl, may form an oxazole, triazole, tetrazole, triazine, tetrazine, thiomorpholine, imidazole, thiazole, thiadiazole, pyrimidine, pyrazine, pyridazine, piperazine or N-substituted piperazine ring, where the nitrogen of the group —N(R4)R5 in such unsaturated rings may optionally form a double bond to one of the substituents R4, R5 and may therefore be in quaternized form in the group —N(R4)R5,
  or where d can be
    a 3-7-membered saturated or unsaturated nitrogen heterocycle whose bond to the component a, b or c of the substituent S1, S2, S3 or S4 is via a ring carbon, preferably an azirine, aziridine, azete, dihydroazete, azetidine, pyrrole, pyrrolidine, pyridine, piperidine, azepine, azepan heterocycle,
    or a 5-8-membered saturated or unsaturated heterocycle comprising N and one or more further unsubstituted or substituted heteroatoms from the group —O—, —S—, —NH—, —N(R7)- where R7=H, straight-chain or branched $C_1$-$C_{20}$ alkyl, aralkyl, alkylaryl, cycloalkyl, whose bond to the component a, b or c of the substituent S1, S2, S3 or S4 is via a ring carbon, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine heterocycle, and also cationic derivatives and saturated derivatives of these polymers.

The formulae 1 and 2 embrace all of the stereoisomeric forms of the structural units shown.

In formula 1 the ring containing the ring member X1 is a ring from the group consisting of cyclopentane, cyclohexane tetrahydrofuran, tetrahydrothiophene, pyrrolidine, N-substituted pyrrolidine ring, exocyclically substituted or unsubstituted endocyclically saturated fulvene ring, phospholane ring, P-substituted phospholane ring.

For n=0 the ring containing the ring member X1 carries the substituents S1, S2, S3, S4. For n=1, X1 and X2 can be identical or different, and fused onto the ring carrying the ring member X1 is either a 7-membered norbornene ring, a norbornene derivative or, if X2 is —$CH_2$—$CH_2$—, an 8-membered bicycle. This bicycle containing the ring member X2 carries the substituents S1, S2, S3, S4.

In formula 2 the ring containing the ring member X1 is part of a 7-membered norbornene ring, a norbornene derivative or, if X2 is —$CH_2$—$CH_2$—, part of an 8-membered bicycle.

For n=0 the ring containing the ring member X1 carries the substituents S1, S2, S3, S4. For n=1, X1 and X2 can be identical or different, and fused onto the bicycle carrying the ring member X1 is either a 7-membered norbornene ring, a norbornene derivative or, if X2 is —$CH_2$—$CH_2$—, an 8-membered bicycle. This bicycle containing the ring member X2 carries the substituents S1, S2, S3, S4.

The term norbornene derivative also embraces 7-membered carbon bicycles, having two 2-membered bridges and one 1-membered bridge, in which the 1-membered bridge is formed by a heteroatom.

For formula 1 and formula 2, n=0 is preferred. If n=1, then in formula 1 and formula 2 preferably X1=X2.

In formula 1 and formula 2 the straight-chain or branched $C_1$-$C_{20}$ alkyl substituents R1, R2, R3 are for example methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl.

At least one of the substituents S1, S2, S3, S4 is -a-d, -a-b-d, -b-c-d, -a-b-c-d.

The substructures -a-d, -a-b-d, -b-c-d or -a-b-c-d which occur in the substituents S1, S2, S3, S4 have a spacer, with -a-, -a-b-, -b-c- or -a-b-c, and, with -d, a terminal functional group. The length, nature, and substitution pattern of the spacer may vary within a wide range. Variation is likewise possible in the substitution pattern of the terminal functional group. As a result the substituents S1, S2, S3, S4 can be custom-tailored to different end applications. In order to optimize the structure of S1, S2, S3, S4 for a certain application, for example, with a given structure of the spacer, it is possible to use a secondary or tertiary terminal amino group having long-chain or short-chain substituents. Likewise, depending on the nature and structure of the terminal amino group, the spacer may have a longer or shorter chain length in order to correspond optimally to a desired end application.

The straight-chain or branched $C_2$-$C_{20}$ alkylenes of the substructure a are for example ethylene, propylene, isopropylene, butylene, isobutylene, tert-butylene, pentylene, isopentylene, neopentylene, hexylene, isohexylene, 2-methylpentylene, heptylene, isoheptylene, octylene, 2-ethylhexylene, nonylene, isononylene, decylene, 2-propylheptylene, undecylene, dodecylene, 2-butyloctylene, tridecylene, tetradecylene, 2-pentylnonylene, pentadecylene, hexadecylene, 2-hexyldecylene, heptadecylene, octadecylene, 2-heptylundecylene, nonadecylene, eicosylene, 2-octyldodecylene.

The straight-chain or branched $C_1$-$C_{20}$ alkylenes of substructure c are for example methylene and also the alkylenes stated for substructure a.

With regard to the substituents of the alkylene groups of the substructures a and c, halogen means, for example, F and Cl. The alkylene groups may be partly or fully halogenated. By oxymethylene or polyoxymethylene of substructures a and c is meant, for example, —O—$CH_2$—, —O—$CH_2$—O—$CH_2$—, —O—$CH_2$—O—$CH_2$—O—$CH_2$—, and generally —(O—$CH_2$)$_k$— where k=1-20.

By $C_2$-$C_4$-alkylene glycol or $C_2$-$C_4$-polyalkylene glycol of substructures a and c is meant, for example, ethylene glycol, propylene glycol, butylene glycol, polyethylene glycol, polypropylene glycol, polybutylene glycol.

By cycloalkylenes is meant in the substructures a and c, for example, cyclopentylene, cyclohexylene, cycloheptylene.

By aralkylene is meant in the substructures a and c, for example, benzylene, phenylethylene.

By alkylarylene is meant in the substructures a and c, for example, nonylphenylene.

By arylene is meant in the substructures a and c, for example, phenylene, naphthylene.

By alkylenearylene is meant in the substructures a and c, for example, the structure —$CH_2$-phenylene-, methylenephenylene.

By arylenealkylene is meant in the substructures a and c, for example, the structure -phenylene-$CH_2$—, phenylenemethylene.

The substructure b in the substructures -a-b-d and -a-b-c-d serves as a bridge for the linking of the spacer parts a, c or d with one another, and in the substructure -b-c-d it serves as a bridge for the linking of the entire substituents S1, S2, S3, S4 to the ring of the formulae 1 and 2 that contains the ring member X1 or X2.

Employed for this purpose are, for example, ester, ether, thioether, sulfone, sulfoxide, substituted amino, carbonic diester, thiocarbonic diester, urea, thiourea, urethane, thiourethane, guanidine bridges; the nature of the bridges can be chosen in accordance with the desired field of application of the biocidal polymer.

With regard to the substituent R6 of the nitrogen atom of an amino bridge, straight-chain
or branched $C_1$-$C_6$ alkyl means, for example, methyl, ethyl, propyl, isopropyl, butyl, isobutyl, tert-butyl, pentyl, isopentyl, neopentyl, hexyl, isohexyl, 2-methylpentyl, or neohexyl. By aryl in the case of R6 is meant, for example, phenyl, naphthyl, tolyl, xylyl; by aralkyl is meant, for example, benzyl, phenylethyl; and by alkylaryl is meant, for example, nonylphenyl.

In the group -e(R4)R5, e is N or P, this group therefore encompassing primary, secondary, and tertiary amines and phosphines.

In the case of the substituents R4, R5 of the group -e(R4)R5, straight-chain or branched $C_1$-$C_{20}$ alkyl means, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl;
by aryl is meant, for example, phenyl, naphthyl, tolyl, xylyl;
by aralkyl is meant, for example, benzyl, phenylethyl;
and by alkylaryl is meant, for example, nonylphenyl;
by cycloalkyl is meant, for example, cyclopentyl, cyclohexyl, cycloheptyl;
and by heteroaryl is meant, for example, furyl, pyrrolyl, thiophenyl, pyridinyl.

In the rings formed with the N of the group —N(R4)R5, and also in the unsaturated rings formed with the N of the group —N(R4)R5 and also one or more further substituted or unsubstituted heteroatoms, the nitrogen may form a double bond to one of the substituents R4, R5 and may therefore be quaternized in the group —N(R4)R5, such as in a pyridinium ring, for example.

By the rings formed for the radicals R4 and R5 together with the N of the group —N(R4)R5 are meant the azirine, aziridine, azete, dihydroazete, azetidine, pyrrole, pyridine, azepine, azepan ring.

The saturated or unsaturated rings formed with the N of the group —N(R4)R5 and one or more further unsubstituted or substituted heteroatoms from the group —O—, —S—, —NH—, —N(R7)- are meant imidazolidine, pyrazole, pyrazolidine, dihydrothiazole, thiazolidine, isothiazole, dihydroisothiazole, isothiazolidine, oxazole, dihydroxazole, oxazolidine, isoxazole, dihydroisoxazole, isoxazolidine, diazinane, diazepine, diazepan, preferably oxazole, triazole, tetrazole, triazine, tetrazine, thiomorpholine, imidazole, thiazole, thiadiazole, pyrimidine, pyrazine, pyridazine, piperazine or N-substituted piperazine rings.

The heterocycles which are attached by a ring carbon to the components a, b or c of the substituent S1, S2, S3 or S4 may be, for example, pyrrolidine, piperidine, morpholine and also the same compounds stated in the two preceding paragraphs. Heterocycles of this kind are used more preferably in substituents of the type -a-d.

All of the heterocycles stated in the three preceding paragraphs may carry further substituents on the heteroatoms or on the ring carbon atoms, examples being $C_1$-$C_4$ alkyls such as ethyl, propyl, isopropyl, butyl, isobutyl, tert-butyl. One example of such a compound is the 2,2,6,6-tetramethyl-piperidine-4-oxyl radical.

The heterocycles stated in the four preceding paragraphs may also be part of a fused ring system. Examples of compounds of this kind are purine, indole, isoindole, dihydroindole, dihydroisoindole, quinoline, isoquinoline, carbazole, phenazine, phenoxazine, phenothiazine, pterine, pteridine, benzazepine, and also their hydrogenated and part-hydrogenated derivatives.

In the case of the substituent R7 of the further heteroatom N, straight-chain or branched $C_1$-$C_{20}$ alkyl means, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl; aralkyl means, for example, benzyl, phenylethyl;
alkylaryl means, for example, nonylphenyl;
and cycloalkyl means, for example, cyclopentyl, cyclohexyl, cycloheptyl.

By modifying the biocidal polymers it is possible to obtain cationic derivatives and saturated derivatives of the biocidal polymers.

The cationic derivatives of the biocidal polymers may be the protonated compounds or else compounds with quaternized nitrogen or phosphorus. The substituents attached in the case of quaternization may be, for example, $C_1$-$C_{20}$ alkyls such as methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl, aryls such as, for example, phenyl, tolyl, xylyl, naphthyl, aralkyls such as, for example, benzyl, phenylethyl, or alkylaryls such as nonylphenyl. The cationic derivatives may be prepared, for example, by polymer-analogous reaction with dialkyl sulfates, alkyl halides or aralkyl halides.

Biocidal polymers may also take the form of salts of mineral acids such as HCl or HBr, for example, or the form of salts of organic acids such as $CF_3COOH$, for example.

The saturated derivatives of the biocidal polymers can be obtained by aftertreating the double bonds in the polymer chain, such as by hydrogenation, by addition reactions such as epoxidation, chlorination, addition of ammonia, crosslinking copolymerization with vinyl monomers (e.g., styrene, acrylonitrile) or with olefins (e.g., butene) or with acrylates and methacrylates (e.g., butyl acrylate and methyl methacrylate), hydrosilylation, thiol-ene addition reaction, for example.

For the purposes of the present invention the term polymer also embraces oligomers having more than 3 repeating units.

DETAILED DESCRIPTION

The biocidal polymers of claim 1 are based on compounds corresponding to the general formula 3. Accordingly the invention further provides compounds of the general formula 3

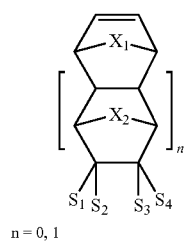

formula 3 n = 0, 1 where X1 and X2 can be identical or different and where X1 and X2 can be
—$CH_2$—, —$CH_2$—$CH_2$—, —O—, —S—, —N(R1)-, —P(R1), =(C=C(R2)R3),
where R1, R2, R3=H, straight-chain or branched $C_1$-$C_{20}$ alkyl, where R2 and R3 can be identical or different,
and where the substituents S1, S2, S3, S4 can be identical or different
where S1, S2, S3, S4=H, straight-chain or branched $C_1$-$C_{20}$ alkyl, cycloalkyl, alkylaryl, aralkyl, aryl, —CO—O—(R9)-NH(tert-butyl), where R9 is an unbranched or branched $C_1$-$C_{20}$ alkylene which optionally is substituted one or more times by one or more halogen groups, preferably a $C_1$-$C_6$ alkylene,
—CO—O—$(CH_2)_2$—NH (n-butyl),
—CO—O—$(CH_2)_3$—NH (n-butyl),
—CO—O—$(CH_2)_4$—NH (n-butyl),
—CO—O-(3-(dimethylamino)phenyl),
—CO—O—$(CH_2)_2$-(4-(dimethylamino)phenyl,
—CO—O—$(CH_2)_2$-(1-piperazinyl),
—CO—O-(2-pyridyl),
—CO—O-(3-pyridyl),
—CO—O-(4-pyridyl),
—CO—O-(2-piperidyl),
—CO—O-(3-piperidyl),
—CO—O-(4-piperidyl),
—CO—O—$(CH_2)_2$-(3-indolyl)
—CO—O-(4-(2,2,6,6-tetramethyl)-piperidyl),
-phenylene-$CH_2$—O—$(CH_2)_2$—$N(CH_3)_2$, -a-d, -a-b-d, -b-c-d, a-b-c-d,
where at least one of the substituents S1, S2, S3, S4 is not H, straight-chain or branched $C_1$-$C_{20}$ alkyl, cycloalkyl, aralkyl, alkylaryl, aryl,
and where a can be a straight-chain or branched $C_3$-$C_{20}$ alkylene whose two free valences are located at the two ends of a chain of at least 3 C atoms, preferably a $C_3$-$C_6$ alkylene, and which optionally is substituted one or more times by one or more halogen groups,
or a siloxane, an oligo- or polysiloxane having 1-20 repeating units,
or oxymethylene or a polyoxymethylene —$(O—CH_2)_k$— where k=1-20, or a $C_2$-$C_4$ alkylene glycol or $C_2$-$C_4$ polyalkylene glycol having 1-20 repeating units, or a cycloalkylene,
or an aralkylene whose two free valences are located at the two ends of a chain of at least 3 C atoms,
or an alkylarylene,
or an arylene,
or an alkylenearylene,
or an arylenealkylene,
and where b can be —O—, —O—CO—, —O—CO—O—, —CO—, —NH—CO—, —S—, —$SO_2$—, —SO—, —O—CS—O—, —N(R6)- where R6=H, straight-chain or branched $C_1$-$C_6$ alkyl, aryl, aralkyl, —O—CO—NH—, —NH—CO—NH—, —O—CS—NH—, —NH—CS—NH—, —NH—C(NH)—NH—, —NH—CO—O—, —NH—CS—O—,
and where c can be a straight-chain or branched $C_1$-$C_{20}$ alkylene, preferably $C_1$-$C_6$ alkylene, which optionally is substituted one or more times by one or more halogen groups,
or a siloxane, an oligo- or polysiloxane having 1-20 repeating units,
or oxymethylene or a polyoxymethylene —$(O—CH_2)_k$— where k=1-20,
or a $C_2$-$C_4$ alkylene glycol or $C_2$-$C_4$ polyalkylene glycol having 1-20 repeating units, or a cycloalkylene,
or an aralkylene,
or an alkylarylene,
or an arylene,
or an alkylenearylene,
or an arylenealkylene,
and where d can be
-e(R4)R5 with e=N or P,
where the group -e(R4)R5 can be a guanidinyl radical —NH—C(NH)—$NH_2$, an N-substituted gyanidinyl radical, a biguanidinyl radical, a hydrazinyl radical —NH—$NH_2$ or an N-substituted hydrazinyl radical,
and where, in the group -e(R4)R5,
the radicals R4 and R5 can be identical or different
where R4, R5=H, straight-chain or branched $C_1$-$C_{20}$ alkyl, aralkyl, alkylaryl, aryl, cycloalkyl, heteroaryl,
or the radicals R4 and R5
together with N of the group —N(R4)R5 can form a 3-7-membered saturated or unsaturated ring, preferably an azirine, aziridine, azete, dihydroazete, azetidine, pyrrole, pyrrolidine, pyridine, piperidine, azepine, azepan ring, or together with N of the group —N(R4)R5 and with one or more further unsubstituted or substituted heteroatoms from the group —O—, —S—, —NH—, —N(R7)- where R7=H, straight-chain or branched $C_1$-$C_{20}$ alkyl, aralkyl, cycloalkyl, can form a 5-8-membered saturated or unsaturated ring, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine ring, where the nitrogen of the group —N(R4)R5 in such 3-7-membered and 5-8-membered unsaturated rings may optionally form a double bond to one of the substituents R4, R5 and may therefore be in quaternized form in the group —N(R4)R5, or where d can be a 3-7-membered saturated or unsaturated nitrogen heterocycle whose bond to the component a, b or c of the substituent S1, S2, S3 or S4 is via a ring carbon, preferably an azirine, aziridine, azete, dihydroazete, azetidine, pyrrole, pyrrolidine, pyridine, piperidine, azepine, azepan heterocycle, or a 5-8-membered saturated or unsaturated heterocycle comprising N and one or more further unsubstituted or substituted heteroatoms from the group —O—, —S—, —NH—, —N(R7)- where R7=H, straight-chain or branched $C_1$-$C_{20}$ alkyl, aralkyl, aryl, alkylaryl, cycloalkyl, whose bond to the component a, b or c of the substituent S1, S2, S3 or S4 is via a ring carbon, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine heterocycle.

Preference is given to compounds of the general formula 3 where X1 and X2 can be identical or different and where X1 and X2 can be

—CH$_2$—, —CH$_2$—CH$_2$—, —O—, —S—, —N(R1)-; —P(R1)-, =(C=C(R2)R3), where R1, R2, R3=H, straight-chain or branched $C_1$-$C_{20}$ alkyl, where R2 and R3 can be identical or different, and where the substituents S1, S2, S3, S4 can be identical or different, where S1, S2, S3, S4=H, -b-c-NH-tert-butyl, -phenylene-CH$_2$—O— (CH$_2$)$_2$—N(CH$_3$)$_2$, where at least one of the substituents S1, S2, S3, S4 is -b-c-NH-tert-butyl or -phenylene-CH$_2$—O— (CH$_2$)$_2$—N(CH$_3$)$_2$ and where b can be —O—, —O—CO—, —O—(CH$_2$)$_n$— where n=1-6, and where c can be a straight-chain or branched $C_1$-$C_{20}$ alkylene, preferably $C_1$-$C_6$ alkylene, which optionally is substituted one or more times by one or more halogen groups.

The formula 3 embraces all of the stereoisomeric forms of the structure shown.

In formula 3 the ring containing the ring member X1 is part of a 7-membered norbornene ring, a norbornene derivative or, if X2 is —CH$_2$—CH$_2$—, part of an 8-membered bicycle.

For n=0 the ring containing the ring member X1 carries the substituents S1, S2, S3, S4. For n=1, X1 and X2 can be identical or different, and fused onto the bicycle carrying the ring member X1 is either a 7-membered norbornene ring, a norbornene derivative or, if X2 is —CH$_2$—CH$_2$—, an 8-membered bicycle. This bicycle containing the ring member X2 carries the substituents S1, S2, S3, S4.

The term norbornene derivative also embraces 7-membered carbon bicycles, having two 2-membered bridges and one 1-membered bridge, in which the 1-membered bridge is formed by a heteroatom.

For formula 3, n=0 is preferred. If n=1, then in formula 3 preferably X1=X2.

In formula 3 the straight-chain or branched $C_1$-$C_{20}$ alkyl substituents R1, R2, R3 on N, P or the exocyclic double bond of the endocyclically saturated fulvene ring are for example methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, noradecyl, eicosyl, 2-octyldodecyl.

In formula 3 the straight-straight or branched $C_1$-$C_{20}$ alkylenes of the radical R9 are, for example, methylene, ethylene, propylene, isopropylene, butylene, isobutylene, tert-butylene, pentylene, isopentylene, neopentylene, hexylene, isohexylene, 2-methylpentylene, heptylene, isoheptylene, octylene, 2-ethylhexylene, nonylene, isononylene, decylene, 2-propylheptylene, undecylene, dodecylene, 2-butyloctylene, tridecylene, tetradecylene, 2-pentylnonylene, pentadecylene, hexadecylene, 2-hexyldecylene, heptadecylene, octadecylene, 2-heptylundecylene, nonadecylene, eicosylene, 2-octyldecylene.

At least one of the substituents S1, S2, S3, S4 is not H, straight-chain or branched $C_1$-$C_{20}$ alkyl, cycloalkyl, aralkyl, alkylaryl, aryl.

The substituents S1, S2, S3, S4 have a spacer and also a terminal functional group.

By way of example the substructures -a-d, -a-b-d, -b-c-d or -a-b-c-d have a spacer, with -a-, -a-b-, -b-c- or -a-b-c, and, with -d, a terminal functional group. The length, nature, and substitution pattern of the spacer may vary within a wide range. Variation is likewise possible in the substitution pattern of the terminal functional group.

As a result the substituents S1, S2, S3, S4 can be custom-tailored to different end applications. In order to optimize the structure of S1, S2, S3, S4 for a certain application, for example, with a given structure of the spacer, it is possible to use a secondary or tertiary terminal amino group having long-chain or short-chain substituents. Likewise, depending on the nature and structure of the terminal amino group, the spacer may have a longer or shorter chain length in order to correspond optimally to a desired end application.

The straight-chain or branched $C_3$-$C_{20}$ alkylenes of the substructure a are for example propylene, butylene, isobutylene, pentylene, isopentylene, neopentylene, hexylene, isohexylene, 2-methylpentylene, heptylene, isoheptylene, octylene, 2-ethylhexylene, nonylene, isononylene, decylene, 2-propylheptylene, undecylene, dodecylene, 2-butyloctylene, tridecylene, tetradecylene, 2-pentylnonylene, pentadecylene, hexadecylene, 2-hexyldecylene, heptadecylene, octadecylene, 2-heptylundecylene, nonadecylene, eicosylene, 2-octyldodecylene.

The straight-chain or branched $C_1$-$C_{20}$ alkylenes of substructure c are for example methylene, ethylene, isopropylene, tert-butylene and also the alkylenes stated for substructure a.

With regard to the substituents of the alkylene groups of the substructures a and c, halogen means, for example, F and Cl.

The alkylene groups may be partly or fully halogenated. By oxymethylene or polyoxymethylene of substructures a and c is meant, for example, —O—CH$_2$—, —O—CH$_2$—O—

CH$_2$—, —O—CH$_2$—O—CH$_2$—O—CH$_2$—, and generally —(O—CH$_2$)$_k$— where k=1-20.

By C$_2$-C$_4$-alkylene glycol or C$_2$-C$_4$-polyalkylene glycol of substructures a and c is meant, for example, ethylene glycol, propylene glycol, butylene glycol, polyethylene glycol, polypropylene glycol, polybutylene glycol.

By cycloalkylenes is meant in the substructures a and c, for example, cyclopentylene, cyclohexylene, cycloheptylene.

By aralkylene is meant in the substructure a, for example, phenylpropylene.

By aralkylene is meant in the substructure c, for example, benzylene, phenylethylene.

By alkylarylene is meant in the substructures a and c, for example, nonylphenylene.

By arylene is meant in the substructures a and c, for example, phenylene, naphthylene.

By alkylenearylene is meant in the substructures a and c, for example, the structure —CH$_2$-phenylene-, methylenephenylene.

By arylenealkylene is meant in the substructures a and c, for example, the structure -phenylene-CH$_2$—, phenylenemethylene.

The substructure b in the substructures -a-b-d and -a-b-c-d serves as a bridge for the linking of the spacer parts a, c or d with one another, and in the substructure -b-c-d it serves as a bridge for the linking of the entire substituents S1, S2, S3, S4 to the ring of the formula 3 that contains the ring member X1 or X2.

Employed for this purpose are, for example, ester, ether, thioether, sulfone, sulfoxide, substituted amino, carbonic diester, thiocarbonic diester, urea, thiourea, urethane, thiourethane, guanidine bridges; the nature of the bridges can be chosen in accordance with the desired field of application of the biocidal polymer.

With regard to the substituent R6 of the nitrogen atom of an amino bridge, straight-chain or branched C$_1$-C$_6$ alkyl means, for example, methyl, ethyl, propyl, isopropyl, butyl, isobutyl, tert-butyl, pentyl, isopentyl, neopentyl, hexyl, isohexyl, 2-methylpentyl, or neohexyl. By aryl in the case of R6 is meant, for example, phenyl, naphthyl, tolyl, xylyl; by aralkyl is meant, for example, benzyl, phenylethyl; and by alkylaryl is meant, for example, nonylphenyl.

In the group -e(R4)R5, e is N or P, this group therefore encompassing primary, secondary, and tertiary amines and phosphines.

In the case of the substituents R4, R5 of the groups —P(R4)R5 and —N(R4)R5, straight-chain or branched C$_1$-C$_{20}$ alkyl means, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl; by aryl is meant, for example, phenyl, naphthyl, tolyl, xylyl;
by aralkyl is meant, for example, benzyl, phenylethyl;
and by alkylaryl is meant, for example, nonylphenyl;
by cycloalkyl is meant, for example, cyclopentyl, cyclohexyl, cycloheptyl;
and by heteroaryl is meant, for example, furyl, pyrrolyl, thiophenyl, pyridinyl.

In the 3-7-membered unsaturated rings formed with the N of the group —N(R4)R5, and also in the 5-8-membered unsaturated rings formed with the N of the group —N(R4)R5 and also a further heteroatom, the nitrogen may form a double bond to one of the substituents R4, R5 and may therefore be quaternized in the group —N(R4)R5, such as in a pyridinium ring, for example.

By the 3-7-membered saturated or unsaturated heterocycles formed with the N of the group —N(R4)R5 are preferably meant the azirine, aziridine, azete, dihydroazete, azetidine, pyrrole, pyrrolidine, pyridine, piperidine, azepine, azepan ring.

By the 5-8-membered saturated or unsaturated heterocycles formed with the N of the group —N(R4)R5 and one or more further unsubstituted or substituted heteroatoms from the group —O—, —S—, —NH—, —N(R7)- are meant imidazolidine, pyrazole, pyrazolidine, dihydrothiazole, thiazolidine, isothiazole, dihydroisothiazole, isothiazolidine, oxazole, dihydroxazole, oxazolidine, isoxazole, dihydroisoxazole, isoxazolidine, diazinane, diazepine, diazepan, preferably oxazole, triazole, tetrazole, triazine, tetrazine, morpholine, thiomorpholine, imidazole, thiazole, thiadiazole, pyrimidine, pyrazine, pyridazine, piperazine or N-substituted piperazine rings.

The heterocycles which are attached by a ring carbon to the components a, b or c of the substituent S1, S2, S3 or S4 may be, for example, the same compounds stated in the two preceding paragraphs. Heterocycles of this kind are used more preferably in substituents of the type -a-d.

All of the heterocycles stated in the three preceding paragraphs may carry further substituents on the heteroatoms or on the ring carbon atoms, examples being C$_1$-C$_4$ alkyls such as ethyl, propyl, isopropyl, butyl, isobutyl, tert-butyl. One example of such a compound is the 2,2,6,6-tetramethyl-piperidine-4-oxyl radical.

The heterocycles stated in the four preceding paragraphs may also be part of a fused ring system. Examples of compounds of this kind are purine, indole, isoindole, indazole, dihydroindole, dihydroisoindole, quinoline, isoquinoline, carbazole, phenazine, phenoxazine, phenothiazine, pterine, pteridine, benzazepine, and also their hydrogenated and part-hydrogenated derivatives.

In the case of the substituent R7 of the further heteroatom N in a 5-8-membered ring, the straight-chain or branched C$_1$-C$_{20}$ alkyls mean, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl; aralkyl means, for example, benzyl, phenylethyl; alkylaryl means, for example, nonylphenyl; and cycloalkyl means, for example, cyclopentyl, cyclohexyl, cycloheptyl.

Particularly preferred compounds are
exo,endo-bicyclo[2.2.1]hept-5-ene-2-carboxylic acid 2-tert-butylaminoethyl ester and also
(+/−)exo,endo-bicyclo[2.2.1]hept-5-ene-2,3-dicarboxylic acid bis(2-tert-butylaminoethyl) ester.

The compounds of the general formula 3 are valuable intermediates for the preparation of biocidal polymers of claim 1.

The invention further provides for the use of compounds of the general formula 3, formula 3

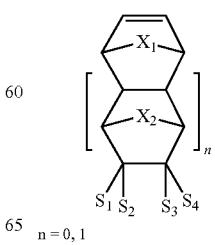

n = 0, 1 for preparing biocidal polymers,
where X1 and X2 can be identical or different and where X1 and X2 can be
—$CH_2$—, —$CH_2$—$CH_2$—, —O—, —S—, —N(R1)-, —P(R1)-, =(C=C(R2)R3),
where R1, R2, R3=H, straight-chain or branched $C_1$-$C_{20}$ alkyl, where R2 and R3 can be identical or different,
and where the substituents S1, S2, S3, S4 can be identical or different
where S1, S2, S3, S4=H, straight-chain or branched $C_1$-$C_{20}$ alkyl, cycloalkyl, aralkyl, alkylaryl, aryl, -a-d, -a-b-d, -b-c-d, -a-b-c-d,
where at least one of the substituents S1, S2, S3, S4 is a-d, -a-b-d, -b-c-d, -a-b-c-d,
and where a can be a straight-chain or branched $C_3$-$C_{20}$ alkylene, preferably $C_3$-$C_6$ alkylene which optionally is substituted one or more times by one or more halogen groups,
or a siloxane, an oligo- or poly-siloxane having 1-20 repeating units,
or oxymethylene or a polyoxymethylene —(O—$CH_2$)$_k$— where k=1-20, or a $C_2$-$C_4$ alkylene glycol or $C_2$-$C_4$ polyalkylene glycol having 1-20 repeating units,
or a cycloalkylene,
or an aralkylene,
or an alkylarylene,
or an arylene,
or an alkylenearylene,
or an arylenealkylene,
and where b can be —O—, —O—CO—, —CO—C—, —O—CO—O—, —CO—, —CO—NH—, —NH—CO—, —S—, —$SO_2$—, —SO—, —O—CS—O—, —N(R6)- where R6=H, straight-chain or branched $C_1$-$C_6$ alkyl, aryl, aralkyl, alkylaryl, —O—CO—NH—, —NH—CO—NH—, —O—CS—NH—, —NH—CS—NH—, —NH—C(NH)—NH, —NH—CO—O, —NH—CS—O—,
and where c can be a straight-chain or branched $C_1$-$C_{20}$ alkylene, preferably $C_1$-$C_6$ alkylene, which optionally is substituted one or more times by one or more halogen groups,
or a siloxane, an oligo- or poly-siloxane having 1-20 repeating units,
or oxymethylene or a polyoxymethylene —(O—$CH_2$)$_k$— where k=1-20,
or a $C_2$-$C_4$ alkylene glycol or $C_2$-$C_4$ polyalkylene glycol having 1-20 repeating units
or a cycloalkylene,
or an aralkylene,
or an alkylarylene,
or an arylene,
or an alkylenearylene,
or an arylenealkylene,
and where d can be
-e (R4)R5 with e=N or P,
where the group -e(R4)R5 can be a guanidinyl radical —NH—C(NH)—$NH_2$, an N-substituted gyanidinyl radical, a biguanidinyl radical, a hydrazinyl radical —NH—$NH_2$ or an N-substituted hydrazinyl radical,
and where, in the group -e(R4)R5,
the radicals R4 and R5 can be identical or different
where R4, R5=H, straight-chain or branched $C_1$-$C_{20}$ alkyl, aralkyl, alkylaryl, aryl, cycloalkyl, heteroaryl,
or the radicals R4 and R5
together with N of the group —N(R4)R5 can form a 3-7-membered saturated or unsaturated ring, preferably an azirine, aziridine, azete, dihydroazete, azetidine, pyrrole, pyrrolidine, pyridine, piperidine, azepine, azepan ring,
or together with N of the group —N(R4)R5 and with one or more further unsubstituted or substituted heteroatoms from the group —O—, —S—, —NH—, —N(R7)-
where R7=H, straight-chain or branched $C_1$-$C_{20}$ alkyl, aralkyl, cycloalkyl, can form a 5-8-membered saturated or unsaturated ring, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine ring,
where the nitrogen of the group —N(R4)R5 in such 3-7-membered and 5-8-membered unsaturated rings may optionally form a double bond to one of the substituents R4, R5 and may therefore be in quaternized form in the group —N(R4)R5,
or where d can be
a 3-7-membered saturated or unsaturated nitrogen heterocycle whose bond to the component a, b or c of the substituent S1, S2, S3 or S4 is via a ring carbon, preferably an azirine, aziridine, azete, dihydroazete, azetidine, pyrrole, pyrrolidine, pyridine, piperidine, azepine, azepan heterocycle,
or a 5-8-membered saturated or unsaturated heterocycle comprising N and one or more further unsubstituted or substituted heteroatoms from the group —O—, —S—, —NH—, —N(R7)- where R7=H, straight-chain or branched $C_1$-$C_{20}$ alkyl, aralkyl, alkylaryl, cycloalkyl, whose bond to the component a, b or c of the substituent S1, S2, S3 or S4 is via a ring carbon, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine heterocycle.

Preference is given to the use of compounds of the general formula 3 for preparing biocidal polymers,
where X1 and X2 can be identical or different and where X1 and X2 can be
—$CH_2$—, —$CH_2$—$CH_2$—, —O—, —S—, —N(R1)-, —P(R1)-, =(C=C(R2)R3),
where R1, R2, R3=H, straight-chain or branched $C_1$-$C_{20}$ alkyl, where R2 and R3 can be identical or different,
and where the substituents S1, S2, S3, S4 can be identical or different,
where S1, S2, S3, S4=H, -b-c-NH-tert-butyl, -phenylene-$CH_2$—O—($CH_2$)$_2$—N($CH_3$)$_2$,
where at least one of the substituents S1, S2, S3, S4 is -b-c-NH-tert-butyl or -phenylene-$CH_2$—O—($CH_2$)$_2$—N($CH_3$)$_2$,
and where b can be —O—, —O—CO—, —CO—O—, —O—($CH_2$)$_n$— where n=1-6,
and where c can be a straight-chain or branched $C_1$-$C_{20}$ alkylene, preferably $C_1$-$C_6$ alkylene, which optionally is substituted one or more times by one or more halogen groups.

The formula 3 embraces all of the stereoisomeric forms of the structure shown.

In formula 3 the ring containing the ring member X1 is part of a 7-membered norbornene ring, a norbornene derivative or, if X2 is —$CH_2$—$CH_2$—, part of an 8-membered bicycle.

For n=0 the ring containing the ring member X1 carries the substituents S1, S2, S3, S4. For n=1, X1 and X2 can be identical or different, and fused onto the bicycle carrying the ring member X1 is either a 7-membered norbornene ring, a norbornene derivative or, if X2 is —$CH_2$—$CH_2$—, an 8-membered bicycle. This bicycle containing the ring member X2 carries the substituents S1, S2, S3, S4.

The term norbornene derivative also embraces 7-membered carbon bicycles, having two 2-membered bridges and one 1-membered bridge, in which the 1-membered bridge is formed by a heteroatom.

For formula 3, n=0 is preferred. If n=1, then in formula 3 preferably X1=X2.

The definition of the substructure a of the substituents S1, S2, S3, S4 corresponds, with the exception of the ethylene group, to the definition of the substructure a of the substituents S1, S2, S3, S4 in the formulae 1 and 2 of claim 1.

The definition of the substructure b and c of the substituents S1, S2, S3, S4 is the same as the definition of the substructures b and c of the substituents S1, S2, S3, S4 in the formulae 1 and 2 of claim 1.

In the substructure d of the substituents S1, S2, S3, S4, e in the group -e(R4)R5 is N or P, as a result of which this group embraces primary, secondary, and tertiary amines and phosphines.

In the case of the substituents R4, R5 of the groups —P(R4)R5 and —N(R4)R5, straight-chain or branched $C_1$-$C_{20}$ alkyl means, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl; by aryl is meant, for example, phenyl, naphthyl, tolyl, xylyl;

by aralkyl is meant, for example, benzyl, phenylethyl; and by alkylaryl is meant, for example, nonylphenyl;

by cycloalkyl is meant, for example, cyclopentyl, cyclohexyl, cycloheptyl;

and by heteroaryl is meant, for example, furyl, pyrrolyl, thiophenyl, pyridinyl.

In the 3-7-membered unsaturated rings formed with the N of the group —N(R4)R5, and also in the 5-8-membered unsaturated rings formed with the N of the group —N(R4)R5 and also a further heteroatom, the nitrogen may form a double bond to one of the substituents R4, R5 and may therefore be quaternized in the group —N(R4)R5, such as in a pyridinium ring, for example.

By the 3-7-membered saturated or unsaturated heterocycles formed with the N of the group —N(R4)R5 are preferably meant the azirine, aziridine, azete, dihydroazete, azetidine, pyrrole, pyrrolidine, pyridine, piperidine, azepine, azepan ring.

By the 5-8-membered saturated or unsaturated heterocycles formed with the N of the group —N(R4)R5 and one or more further unsubstituted or substituted heteroatoms from the group —O—, —S—, —NH—, —N(R7)- are meant, for example, imidazolidine, pyrazole, pyrazolidine, dihydrothiazole, thiazolidine, isothiazole, dihydroisothiazole, isothiazolidine, oxazole, dihydroxazole, oxazolidine, isoxazole, dihydroisoxazole, isoxazolidine, diazinane, diazepine, diazepan, preferably oxazole, triazole, tetrazole, triazine, tetrazine, morpholine, thiomorpholine, imidazole, thiazole, thiadiazole, pyrimidine, pyrazine, pyridazine, piperazine or N-substituted piperazine rings.

The heterocycles which are attached via a ring carbon to the components a, b or c of the substituent S1, S2, S3 or S4 may be, for example, the same compounds stated in the two preceding paragraphs. Heterocycles of this kind are used more preferably in substituents of the type -a-d.

All of the heterocycles stated in the three preceding paragraphs may carry further substituents on the heteroatoms or on the ring carbon atoms, examples being $C_1$-$C_4$ alkyls such as ethyl, propyl, isopropyl, butyl, isobutyl, tert-butyl. One example of such a compound is the 2,2,6,6-tetramethyl-piperidine-4-oxyl radical.

The heterocycles stated in the four preceding paragraphs may also be part of a fused ring system. Examples of compounds of this kind are purine, indole, isoindole, indazole, dihydroindole, dihydroisoindole, quinoline, isoquinoline, carbazole, phenazine, phenoxazine, phenothiazine, pterine, pteridine, benzazepine, and also their hydrogenated and part-hydrogenated derivatives.

In the case of the substituent R7 of the further heteroatom N in a 5-8-membered ring, the straight-chain or branched $C_1$-$C_{20}$ alkyls mean, for example, methyl, ethyl, propyl, isopropyl, butyl, isobutyl, tert-butyl, pentyl, isopentyl, neopentyl, hexyl, isohexyl, 2-methylpentyl, heptyl, isoheptyl, octyl, 2-ethylhexyl, nonyl, isononyl, decyl, 2-propylheptyl, undecyl, dodecyl, 2-butyloctyl, tridecyl, tetradecyl, 2-pentylnonyl, pentadecyl, hexadecyl, 2-hexyldecyl, heptadecyl, octadecyl, 2-heptylundecyl, nonadecyl, eicosyl, 2-octyldodecyl; aralkyl means, for example, benzyl, phenylethyl; alkylaryl means, for example, nonylphenyl; and cycloalkyl means, for example, cyclopentyl, cyclohexyl, cycloheptyl.

The desired substituents S1, S2, S3, S4 in the general formulae 1, 2, and 3 either are introduced during the actual synthesis of the parent bicyclic substructures, through the choice of corresponding reactants, or are obtained in the completed bicyclic substructures or in the polymer by modification of substituents present.

The compounds of the general formula 3 of claims 3 to 6 serve for preparing biocidal polymers of claim 1. By a biocidal activity is meant in this context the destruction or the inhibition of growth of microorganisms such as bacteria, algae, fungi, and yeasts, for example. The biocidal polymers are thermally stable.

The biocidal polymers may be not only homopolymers but also copolymers. The copolymers may take the form of random copolymers, alternating copolymers, block copolymers or grafted copolymers (graft copolymers).

In the copolymers there may be different structural units of formula 1 linked to one another; there may also be structural units of formula 1 linked to other kinds of structural units. Such other kinds of structural units may be introduced, for example, by copolymerization with unsubstituted norbornene or substituted norbornene derivatives.

Additionally in the copolymers there may be different structural units of formula 2 linked to one another; additionally, structural units of formula 2 may also be linked to other kinds of structural units. Such other kinds of structural units may be introduced, for example, by copolymerization with ethylene, propylene, butylene, unsubstituted norbornene, substituted norbornene derivatives, vinyl monomers such as, for example, styrene and acrylonitrile, acrylates or methacrylates.

For preparing graft copolymers it is possible to proceed by the method of "grafting from" or "grafting to". In the case of "grafting from" the polymerization of the monomer in question begins on an existing substrate polymer B, this substrate polymer B being in solution or in solid form. In the case of "grafting to", an existing polymer A is coupled to a substrate polymer B, and a covalent bond is formed. The substrate polymer B can in this case be in solution or in solid form.

In one particular embodiment of "grafting from" the surface of the substrate polymer B must be activated beforehand (for example, by means of ionizing radiation, UV light, attachment of an initiator or a catalyst) and then the polymerization of the monomer in question must be started on this activated surface.

In this way it is possible to couple biocidal polymers to another surface, thereby giving that surface a biocidal quality.

In a further embodiment ("grafting from") a polymer surface which contains C=C double bonds is provided with a catalyst, which in a further step polymerizes monomers of formula 3 of claim 5 onto this surface. In this case as well a modified surface having biocidal qualities is obtained. For example, norbornene derivatives can be subjected to ring-opening grafting, using ruthenium-carbene complexes, onto surfaces of EPDM rubber (terpolymer containing ethylene, propylene, and a diene monomer).

Both these embodiments give graft copolymers according to claim 7.

In this way the surfaces of plastics and other materials are modified in such a way that these surfaces obtain biocidal qualities, without any need for the materials themselves to be modified in their entirety.

Biocidal polymers may also take the form of blends, composed of two or more biocidal polymers of claim 1 or of one or more biocidal polymers of claim 1 and one or more further polymers.

Examples of further polymers which can be used include polyurethanes, polyolefins, polyethylenes, polypropylenes, polysiloxanes, polystyrenes, poly(alpha-methylstyrenes), polyacrylates, polymethyl methacrylates, PVC, polyamides or polyterephthalates. Particular preference is given to polyethylenes, polypropylenes, and PVC.

The biocidal polymers and polymer blends of the invention may also comprise additives such as, for example, stabilizers, processing assistants, antistats, plasticizers, nucleating agents, dyes and pigments, flame retardants, and antioxidants, and also fillers and reinforcing agents such as nanoparticles, inorganic fibers such as glass fibers or carbon fibers, and organic fibers such as flax, for example (composites).

In order to ensure that a polymer blend has a sufficient biocidal activity, the fraction of biocidal polymer in the blend is 0.2-90% by weight, preferably 1-35% by weight, more preferably 3-10% by weight, based on the total mass of the blend. In specific embodiments of the invention the minimum amount of biocidal polymer may also be 1.5% by weight, preferably 5% by weight, more preferably 7% by weight. The upper limit on the proportion of biocidal polymer may also adopt values up to 40% by weight, more preferably up to 60% by weight, and very preferably up to 80% by weight.

The biocidal polymers are prepared from compounds of the general formula 3 of claim 5 or 6 using a ring-opening metathesis polymerization (ROMP), an addition polymerization via the C=C double bond, with retention of the ring structure, or else a free radical or cationic polymerization.

Examples of catalysts used for metathesis polymerizations include homogeneous catalysts based on ruthenium-carbene complexes and molybdenum-carbene complexes (Love et al., *Angew. Chem.*, 2002, 114(21), 4207-4209).

In order to avoid leaching of the biocidal polymers from the products manufactured from them, polymer structures are used which are extremely insoluble in aqueous systems. For applications where solubility of the polymers in aqueous systems is desired, it is also possible to choose a polymer structure which is soluble in aqueous systems.

The invention further provides for the use of biocidal polymers comprising structural repeating units according to at least one of the formulae 1 and 2

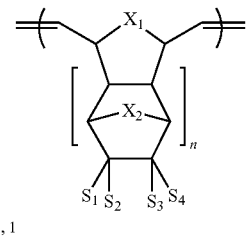

formula 1 n = 0, 1

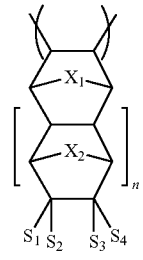

formula 2 n = 0, 1 where X1 and X2 can be identical or different and where X1 and X2 can be
—CH$_2$—, —CH$_2$—CH$_2$—, —O—, —S—, —N(R1)-, —P(R1)-, =(C=C(R2)R3),
with R1, R2, R3=H, straight-chain or branched C$_1$-C$_{20}$ alkyl, where R2 and R3 can be identical or different,
and where the substituents S1, S2, S3, S4 can be identical or different
where S1, S2, S3, S4=H, straight-chain or branched C$_1$-C$_{20}$ alkyl, cycloalkyl, aralkyl, alkylaryl, aryl, -a-d, -a-b-d, -b-c-d, -a-b-c-d,
where at least one of the substituents S1, S2, S3, S4 is a-d, -a-b-d, -b-c-d, -a-b-c-d
and where a can be a straight-chain or branched C$_1$-C$_{20}$ alkylene, preferably C$_2$-C$_{20}$ alkylene, more preferably C$_2$-C$_6$ alkylene which optionally is substituted one or more times by one or more halogen groups,
or a siloxane, an oligo- or poly-siloxane having 1-20 repeating units,
or oxymethylene or a polyoxymethylene —(O—CH$_2$)$_k$— where k=1-20,
or a C$_2$-C$_4$ alkylene glycol or C$_2$-C$_4$ polyalkylene glycol having 1-20 repeating units,
or a cycloalkylene,
or an aralkylene,
or an alkylarylene,
or an arylene,
or an alkylenearylene,
or an arylenealkylene,
and where b can be —O—, —O—CO—, —CO—O—, —O—CO—O—, —CO—, —CO—NH—, —NH—CO—, —S—, —SO$_2$—, —SO—, —O—CS—O—, —N(R6)- where R6=H, straight-chain or branched C$_1$-C$_6$ alkyl, aryl, aralkyl, alkylaryl, —O—CO—NH—, —NH—CO—NH—, —O—CS—NH—, —NH—CS—NH—, —NH—C(NH)—NH, —NH—CO—O—, —NH—CS—O—,
and where c can be a straight-chain or branched C$_1$-C$_{20}$ alkylene, preferably C$_1$-C$_6$ alkylene, which optionally is substituted one or more times by one or more halogen groups,
or a siloxane, an oligo- or poly-siloxane having 1-20 repeating units, or oxymethylene or a polyoxymethylene —(O—CH$_2$)$_k$— where k=1-20,
or a C$_2$-C$_4$ alkylene glycol or C$_2$-C$_4$ polyalkylene glycol having 1-20 repeating units
or a cycloalkylene,
or an aralkylene,
or an alkylarylene,
or an arylene,
or an alkylenearylene,
or an arylenealkylene,
and where d can be
-e(R4)R5 where e=N or P,
where the group -e(R4)R5 can be a guanidinyl radical —NH—C(NH)—NH$_2$, an N-substituted gyanidinyl radical, a biguanidinyl radical, a hydrazinyl radical —NH—NH$_2$ or an N-substituted hydrazinyl radical,
and where, in the group -e(R4)R5,
the radicals R4 and R5 can be identical or different
where R4, R5=H, straight-chain or branched C$_1$-C$_{20}$ alkyl, aralkyl, alkylaryl, aryl, cycloalkyl, heteroaryl,
or the radicals R4 and R5
together with N of the group —N(R4)R5 can form an azirine, aziridine, azete, dihydroazete, azetidine, pyrrole, pyridine, azepine or azapan ring, where the nitrogen of the group —N(R4)R5 in such unsaturated rings may optionally form a double bond to one of the substituents R4, R5 and may therefore be in quaternized form in the group —N(R4)R5,
or together with N of the group —N(R4)R5 and with one or more further unsubstituted or substituted heteroatoms from the group —O—, —S—, —NH—, —N(R7)-
where R7=H, straight-chain or branched C$_1$-C$_{20}$ alkyl, aralkyl, alkylaryl, cycloalkyl, may form an oxazole, triazole, tetrazole, triazine, tetrazine, thiomorpholine, imidazole, thiazole, thiadiazole, pyrimidine, pyrazine, pyridazine, piperazine or N-substituted piperazine ring, where the nitrogen of the group —N(R4)R5 in such unsaturated rings may optionally form a double bond to one of the substituents R4, R5 and may therefore be in quaternized form in the group —N(R4)R5,
or where d can be
a 3-7-membered saturated or unsaturated nitrogen heterocycle whose bond to the component a, b or c of the substituent S1, S2, S3 or S4 is via a ring carbon, preferably an azirine, aziridine, azete, dihydroazete, azetidine, pyrrole, pyrrolidine, pyridine, piperidine, azepine, azepan heterocycle,
or a 5-8-membered saturated or unsaturated heterocycle comprising N and one or more further unsubstituted or substituted heteroatoms from the group —O—, —S—, —NH—, —N(R7)- where R7=H, straight-chain or branched C$_1$-C$_{20}$ alkyl, aralkyl, alkylaryl, cycloalkyl, whose bond to the component a, b or c of the substituent S1, S2, S3 or S4 is via a ring carbon, preferably an oxazole, triazole, tetrazole, triazine, tetrazine, morpholine, thiomorpholine, imidazole, thiazole, thiadiazole, pyrimidine, pyrazine, pyridazine, piperazine or N-substituted piperazine heterocycle, cationic derivatives, and saturated derivatives of these polymers,
or biocidal polymer blends of these polymers and/or their cationic and saturated derivatives, composed of two or more of these biocidal polymers and/or their cationic and saturated derivatives or of one or more of these biocidal polymers and/or their cationic and saturated derivatives and one or more further polymers,
for producing biocidally active products, coatings, surface modifications or medical or cosmetic formulations.

The definition of the substructure a of the substituents S1, S2, S3, S4 corresponds to the definition of the substructure a of the substituents S1, S2, S3, S4 in the formulae 1 and 2 of claim 1, and additionally includes C$_1$ alkylene, by which is meant methylene.

The definition of the substructures b, c, and d of the substituents S1, S2, S3, S4 is the same as the definition of the substructures b, c, and d of the substituents S1, S2, S3, S4 in the formulae 1 and 2 of claim 1.

The biocidally active products may be manufactured from the biocidal polymers or polymer blends themselves, or from polymer mixtures which comprise the biocidal polymers or polymer blends.

They may be, for example, components of systems for storing and conducting drinking water and industrial water, films, fibers, woven fabrics, nonwovens, components of food processing machinery, components of air-conditioning units, components of air-introduction and air-removal systems, components of vehicle interior trim, bathroom and toiletry articles, kitchen articles, components of sanitary installations, components in water systems, toys, food packaging, roofing systems, animal cages, touch panels of instruments, medical articles such as catheters, tubes, films, gloves, caps, patches, blood bags or surgical instruments, hygiene articles such as toothbrushes, toilet seats or combs, and contact lenses.

They may additionally be, for example, containers, storage devices, pumps, and transport lines for food and drink, of the kind used, for example, for applications in the sectors of the food industry, drinks industry, and catering industry.

Where products to be made biocidal have been manufactured from other materials, they may be given the desired biocidal properties by coatings of the biocidal polymers or polymer blends. Such coatings include protective coatings and paint systems in which the polymers or polymer blends are present in dispersed form.

Areas of application for biocidal coatings may be, for example, the sanitary sector, such as toiletry articles, for example; the food sector, such as kitchen articles, for example; drinking-water systems, cosmetics or toys, the home sector, such as wood preservation or roofing systems, parts for refrigerators, dishwashers or washing machines, for example; the marine sector, such as boat hulls, docks, ballast water tanks or drilling platforms, for example; mechanical engineering, such as air-conditioning units, ion exchangers, bioreactors or industrial water plants, for example; the medical engineering sector, such as implants, contact lenses or membranes, for example; or the consumer products sector, such as clothing, carpets, door handles, for example, or hospital equipment. Biocidal coatings may also be applied to paper and packaging materials such as cardboard, for example.

The areas of application for biocidal coatings and biocidal products to a very large extent correspond to one another.

The biocidal polymers and polymer blends can additionally be added as additives to cosmetic or medical formulations in order, for example, to give pastes or ointments with biocidal activity.

Added in dispersed form or in solution, the biocidal polymers and polymer blends may be used for disinfecting, sterilizing, and preventing biofouling in closed or open industrial-water systems and cooling-water systems. The dispersed polymers and polymer blends can be removed from the systems by filtration.

EXAMPLES

The following examples are provided for the purpose of illustrating the invention and are not to be construed as limiting the invention in any manner.

Example 1

Preparation of Monomers 1-4

Monomer 1 exo,endo-Bicyclo[2.2.1]hept-5-ene-2-carboxylic acid 2-(tert-butylamino)ethyl ester 0.160 mol of acryloyl chloride (from Lancaster) was introduced as an initial charge in dilution in 30 ml of dichloromethane. 0.320 mol of freshly cracked cyclopentadiene (bp=41° C.) was added slowly dropwise with stirring in an ice bath. When dropwise addition was complete, the reaction solution was stirred at room temperature for 14 h. The resulting reaction solution of exo,endo-bicyclo[2.2.1]hept-5-ene-2-carbonyl chloride was admixed slowly dropwise, with stirring and in an ice bath, with a solution of 0.144 mol of 2-tert-butylaminoethanol (from Aldrich) in 30 ml of dichloromethane. When dropwise addition was complete, the reaction solution was stirred at room temperature for 24 h. The solvent was stripped off under reduced pressure. The pale yellow residue was reprecipitated from chloroform/n-heptane.

Recrystallization from acetone gave a white solid (hydrochloride). This intermediate was dissolved in 300 ml of chloroform, 0.144 mol of $Na_2CO_3 \cdot H_2O$ was added, and the suspension was stirred at room temperature for 3 h.

Thereafter it was extracted with 150 ml of distilled water. The pH of the aqueous phase was 8. The organic phase was dried over $Na_2SO_4$ and the solvent was removed under reduced pressure. This gave the product as an oily liquid in a yield of 52%.

NMR (1H, 500 MHz, $CDCl_3$, ppm): 6.18, 5.92 (CH=CH in the ring), 2.77 ($CH_2$—NHR)
FTIR (film on CaF2, $cm^{-1}$): 3323 ($R_2NH$), 3062 (=CH— in the ring), 1735 (C=O).

Monomer 2

(+/−)-exo,endo-Bicyclo[2.2.1]hept-5-ene-2,3-dicarboxylic acid bis-2-(tert-butylamino)ethyl ester 0.114 mol of fumaroyl chloride (from Lancaster) was introduced as an initial charge in dilution in 30 ml of dichloromethane. 0.228 mol of freshly cracked cyclopentadiene (bp=41° C.) was added slowly dropwise with stirring in an ice bath. When dropwise addition was complete, the reaction solution was stirred at room temperature for 24 h. The resulting reaction solution of
(+/−)-exo,endo-bicyclo[2.2.1]hept-5-ene-2,3-dicarbonyl dichloride was admixed slowly dropwise, with stirring and in an ice bath, with a solution of 0.210 mol of 2-tert-butylaminoethanol (from Aldrich) in 200 ml of $CH_2Cl_2$. When dropwise addition was complete, the reaction solution was stirred at room temperature for 24 h. The solvent was stripped off under reduced pressure. The white solid was extracted with n-heptane. This intermediate was suspended in 600 ml of chloroform, 0.210 mol of $Na_2CO_3 \cdot H_2O$ was added, and the suspension was stirred at room temperature for 3 h. Thereafter it was extracted with 300 ml of distilled water. The pH of the aqueous phase was 9. The organic phase was dried over $Na_2SO_4$ and the solvent was removed under reduced pressure. This gave the product as an oily liquid in a yield of 61%.

NMR (1H, 500 MHz, $CDCl_3$): 6.26, 6.04 (CH=CH in the ring), 2.78, 2.75 ($CH_2$—NHR)
FTIR (film on CaF2, $cm^{-1}$): 3323 ($R_2NH$), 3063 (=CH— in the ring), 1731 (C=O).

The following compounds were obtained in a similar way:

Monomer 3 exo,endo-Bicyclo[2.2.1]hept-5-ene-2-carboxylic acid 2-(dimethylamino)ethyl ester NMR (1H, 500 MHz, $CDCl_3$, ppm): 6.18, 5.92 (CH=CH in the ring), 2.53 ($CH_2$—$NR_2$)
FTIR (film on CaF2, $cm^{-1}$): 3063 (=CH— in the ring), 1735 (C=O).

Monomer 4

(+/−)-exo,endo-Bicyclo[2.2.1]hept-5-ene-2,3-dicarboxylic acid bis-2-(dimethylamino)ethyl ester NMR (1H, 500 MHz, $CDCl_3$): 6.23, 6.03 (CH=CH in the ring), 2.54, 2.50 ($CH_2$—$NR_2$)
FTIR (film on CaF2, $cm^{-1}$): 3065 (=CH— in the ring), 1732 (C=O).

It is also possible to obtain the following esters:
exo,endo-bicyclo[2.2.1]hept-5-ene-2-carboxylic acid 2-(butylamino)ethyl ester
exo,endo-bicyclo[2.2.1]hept-5-ene-2-carboxylic acid 3-(dimethylamino)phenyl ester
exo,endo-bicyclo[2.2.1]hept-5-ene-2-carboxylic acid 2-[4-dimethylamino)phenyl]ethyl ester
exo,endo-bicyclo[2.2.1]hept-5-ene-2-carboxylic acid 2-(1-piperazino)ethyl ester
exo,endo-bicyclo[2.2.1]hept-5-ene-2-carboxylic acid 2-pyridyl ester
exo,endo-bicyclo[2.2.1]hept-5-ene-2-carboxylic acid 3-pyridyl ester
exo,endo-bicyclo[2.2.1]hept-5-ene-2-carboxylic acid 4-pyridyl ester
exo,endo-bicyclo[2.2.1]hept-5-ene-2-carboxylic acid 2-piperidyl ester
exo,endo-bicyclo[2.2.1]hept-5-ene-2-carboxylic acid 3-piperidyl ester
exo,endo-bicyclo[2.2.1]hept-5-ene-2-carboxylic acid 4-piperidyl ester
exo,endo-bicyclo[2.2.1]hept-5-ene-2-carboxylic acid 2-(3-indolyl)ethyl ester
exo,endo-bicyclo[2.2.1]hept-5-ene-2-carboxylic acid 4-(2,2,6,6-tetramethyl)piperidyl ester
(+/−)-exo,endo-bicyclo[2.2.1]hept-5-ene-2,3-dicarboxylic acid bis-2-(isopropylamino)ethyl ester
(+/−)-exo,endo-bicyclo[2.2.1]hept-5-ene-2,3-dicarboxylic acid bis-2-(diisopropylamino)ethyl ester
(+/−)-exo,endo-bicyclo[2.2.1]hept-5-ene-2,3-dicarboxylic acid bis-3-(dimethylamino)-1-propyl ester
(+/−)-exo,endo-bicyclo[2.2.1]hept-5-ene-2,3-dicarboxylic acid bis-4-(dimethylamino)-1-butyl ester
(+/−)-exo,endo-bicyclo[2.2.1]hept-5-ene-2,3-dicarboxylic acid bis-2-(isopropylamino)ethyl ester
(+/−)-exo,endo-bicyclo[2.2.1]hept-5-ene-2,3-dicarboxylic acid bis-2-(butylamino)ethyl ester
(+/−)-exo,endo-bicyclo[2.2.1]hept-5-ene-2,3-dicarboxylic acid bis-3-(dimethylamino)phenyl ester (+/−)-exo,endo-bicyclo[2.2.1]hept-5-ene-2,3-dicarboxylic acid bis-2[4-(dimethylamino)phenyl]ethyl ester
(+/−)-exo,endo-bicyclo[2.2.1]hept-5-ene-2,3-dicarboxylic acid bis-2-(1-piperazino)ethyl ester
(+/−)-exo,endo-bicyclo[2.2.1]hept-5-ene-2,3-dicarboxylic acid bis-2-pyridyl ester
(+/−)-exo,endo-bicyclo[2.2.1]hept-5-ene-2,3-dicarboxylic acid bis-3-pyridyl ester
(+/−)-exo,endo-bicyclo[2.2.1]hept-5-ene-2,3-dicarboxylic acid bis-4-pyridyl ester
(+/−)-exo,endo-bicyclo[2.2.1]hept-5-ene-2,3-dicarboxylic acid bis-2-piperidyl ester
(+/−)-exo,endo-bicyclo[2.2.1]hept-5-ene-2,3-dicarboxylic acid bis-3-piperidyl ester
(+/−)-exo,endo-bicyclo[2.2.1]hept-5-ene-2,3-dicarboxylic acid bis-4-piperidyl ester
(+/−)-exo,endo-bicyclo[2.2.1]hept-5-ene-2,3-dicarboxylic acid bis-2-(3-indolyl)ethyl ester
(+/−)-exo,endo-bicyclo[2.2.1]hept-5-ene-2,3-dicarboxylic acid bis-4-(2,2,6,6-tetramethyl)piperidyl ester Example 2

Preparation of Polymers 1-4 by Means of ROMP 300 equivalents of monomer are dissolved in 6 ml of absolute (anhydrous) dichloromethane and the solution is introduced in the absence of oxygen into an argon-filled Schlenk vessel. This solution is admixed with a catalyst comprising 1 equivalent of "Bispyridine Complex 6" (Love et al., *Angew. Chem.*, 2002, 114(21), 4207-4209) in solution in 5 ml of absolute dichloromethane, with stirring and the reaction mixture is stirred at room temperature for 24 h in the absence of moisture and oxygen. The reaction is then terminated by addition of 5 drops of ethyl vinyl ether. The reaction solution is concentrated under reduced pressure. The resulting polymer is precipitated from n-pentane and then dried under reduced pressure.

Polymerization of Monomer 1 to Polymer 1

Poly(bicyclo[2.2.1]hept-5-ene-2-carboxylic acid 2-(tert-butylamino)ethyl ester)

Yield 82%
NMR (1H, 500 MHz, CDCl3): 5.33 (CH=CH in main chain), 2.77 ($CH_2$—NHR)
FTIR (film on CaF2, $cm^{-1}$): 3323 ($R_2NH$), 971 (=CH— in main chain), 1729 (C=O)

Polymerization of Monomer 2 to Polymer 2

Poly(bicyclo[2.2.1]hept-5-ene-2,3-dicarboxylic acid bis-2-(tert-butylamino)ethyl ester)

Yield 23%
NMR (1H, 500 MHz, $CDCl^3$): 5.39, 5.22 (CH=CH in main chain), 2.79 ($CH_2$—NHR)
FTIR (film on CaF2, $cm^{-1}$): 3308 ($R_2NH$), 975 (=CH— in main chain), 1729 (C=O)

Polymerization of Monomer 3 to Polymer 3

Poly(bicyclo[2.2.1]hept-5-ene-2-carboxylic acid 2-(dimethylamino)ethyl ester)

Yield 68%
NMR (1H, 500 MHz, CDCl3): 5.31 (CH=CH in main chain), 2.55 ($CH_2$—$NR_2$)
FTIR (film on CaF2, $cm^{-1}$): 2821, 2770 (N—$CH_3$), 969 (=CH— in main chain), 1730 (C=O)

Polymerization of Monomer 4 to Polymer 4

Poly(bicyclo[2.2.1]hept-5-ene-2,3-dicarboxylic acid bis-2-(dimethylamino)ethyl ester)

Yield 61%.
NMR (1H, 500 MHz, CDCl3): 5.39 (CH=CH in main chain), 2.55 ($CH_2$—$NR_2$)
FTIR (film on CaF2, $cm^{-1}$): 2821, 2770 (N—$CH_3$), 970 (=CH— in main chain), 1729 (C=O)

The following polymers can be obtained in a similar way:
poly(bicyclo[2.2.1]hept-5-ene-2-carboxylic acid 2-(diethylamino)ethyl ester)
poly(bicyclo[2.2.1]hept-5-ene-2-carboxylic acid 2-(isopropylamino)ethyl ester)
poly(bicyclo[2.2.1]hept-5-ene-2-carboxylic acid 2-(diisopropylamino)ethyl ester)
poly(bicyclo[2.2.1]hept-5-ene-2-carboxylic acid 3-(dimethylamino)-1-propyl ester)
poly(bicyclo[2.2.1]hept-5-ene-2-carboxylic acid 1-(dimethylamino)-2-propyl ester)
poly(bicyclo[2.2.1]hept-5-ene-2-carboxylic acid 4-(dimethylamino)-1-butyl ester)
poly(bicyclo[2.2.1]hept-5-ene-2-carboxylic acid 2-(butylamino)ethyl ester)
poly(bicyclo[2.2.1]hept-5-ene-2-carboxylic acid 3-(dimethylamino)phenyl ester)
poly(bicyclo[2.2.1]hept-5-ene-2-carboxylic acid 2-[4-(dimethylamino)phenyl]ethyl ester)
poly(bicyclo[2.2.1]hept-5-ene-2-carboxylic acid 2-(4-morpholino)ethyl ester)
poly(bicyclo[2.2.1]hept-5-ene-2-carboxylic acid 2-(1-piperazino)ethyl ester)
poly(bicyclo[2.2.1]hept-5-ene-2-carboxylic acid 2-pyridyl ester)
poly(bicyclo[2.2.1]hept-5-ene-2-carboxylic acid 3-pyridyl ester)
poly(bicyclo[2.2.1]hept-5-ene-2-carboxylic acid 4-pyridyl ester)
poly(bicyclo[2.2.1]hept-5-ene-2-carboxylic acid 2-piperidyl ester)
poly(bicyclo[2.2.1]hept-5-ene-2-carboxylic acid 3-piperidyl ester)
poly(bicyclo[2.2.1]hept-5-ene-2-carboxylic acid 4-piperidyl ester)
poly(bicyclo[2.2.1]hept-5-ene-2-carboxylic acid 2-(3-indolyl)ethyl ester)
poly(bicyclo[2.2.1]hept-5-ene-2-carboxylic acid 4-(2,2,6,6-tetramethyl)piperidyl ester)
poly(bicyclo[2.2.1]hept-5-ene-2,3-dicarboxylic acid bis-2-(diethylamino)ethyl ester)
poly(bicyclo[2.2.1]hept-5-ene-2,3-dicarboxylic acid bis-2-(isopropylamino)ethyl ester)
poly(bicyclo[2.2.1]hept-5-ene-2,3-dicarboxylic acid bis-2-(diisopropylamino)ethyl ester)
poly(bicyclo[2.2.1]hept-5-ene-2,3-dicarboxylic acid bis-3-(dimethylamino)-1-propyl ester)
poly(bicyclo[2.2.1]hept-5-ene-2,3-dicarboxylic acid bis-1-(dimethylamino)-2-propyl ester)
poly(bicyclo[2.2.1]hept-5-ene-2,3-dicarboxylic acid bis-4-(dimethylamino)-1-butyl ester)
poly(bicyclo[2.2.1]hept-5-ene-2,3-dicarboxylic acid bis-2-(isopropylamino)ethyl ester)

poly(bicyclo[2.2.1]hept-5-ene-2,3-dicarboxylic acid bis-2-(butylamino)ethyl ester)

poly(bicyclo[2.2.1]hept-5-ene-2,3-dicarboxylic acid bis-3-(dimethylamino)phenyl ester)

poly(bicyclo[2.2.1]hept-5-ene-2,3-dicarboxylic acid bis-2-[4-(dimethylamino)phenyl]ethyl ester poly(bicyclo[2.2.1]hept-5-ene-2,3-dicarboxylic acid bis-2-(4-morpholino)ethyl ester)

poly(bicyclo[2.2.1]hept-5-ene-2,3-dicarboxylic acid bis-2-(1-piperazino)ethyl ester)

poly(bicyclo[2.2.1]hept-5-ene-2,3-dicarboxylic acid bis-2-pyridyl ester)

poly(bicyclo[2.2.1]hept-5-ene-2,3-dicarboxylic acid bis-3-pyridyl ester)

poly(bicyclo[2.2.1]hept-5-ene-2,3-dicarboxylic acid bis-4-pyridyl ester)

poly(bicyclo[2.2.1]hept-5-ene-2,3-dicarboxylic acid bis-2-piperidyl ester)

poly(bicyclo[2.2.1]hept-5-ene-2,3-dicarboxylic acid bis-3-piperidyl ester)

poly(bicyclo[2.2.1]hept-5-ene-2,3-dicarboxylic acid bis-4-piperidyl ester)

poly(bicyclo[2.2.1]hept-5-ene-2,3-dicarboxylic acid 2-(3-indolyl)ethyl ester)

poly(bicyclo[2.2.1]hept-5-ene-2,3-dicarboxylic acid bis-4-(2,2,6,6-tetramethyl)piperidyl ester)

Example 3

Catalytic Grafting of Monomers 1, 2, 3, and 4 onto EPDM Rubber by Means of ROMP

In preparation the base polymer EPDM rubber (Dutral TER 4049; EPDM terpolymer of 55% ethylene, 40% propylene, and 5% ethylidenenorbornene) is dissolved in toluene and reprecipitated from methanol with 0.1 percent by weight of 3,5-di-tert-butyl-4-hydroxytoluene as stabilizer.

0.2 g of purified EPDM and 0.004 g of 2-hydroxy-2-methyl-1-phenyl-1-propanone (photoinitiator from Ciba) are dissolved in 10 ml of toluene. This solution is applied by means of rotational coating to a $CaF_2$ plaque (Spincoater RC5 from Karl Suess, rotational speed 1000 rpm, rotation time 45 s, rotational acceleration 1000 rpm/s) and irradiated using a mercury vapor lamp under a nitrogen atmosphere for 15 minutes. All further reaction steps take place under an inert gas atmosphere. The specimen obtained is introduced into a round-bottomed flask containing 3 ml of a 0.0015 molar solution of the catalyst "Bispyridine Complex 6" (Love et al., Angew. Chem., 2002, 114(21), 4207-4209) in absolute acetone. After 2 h at 40° C., the specimen is removed and washed with absolute acetone. The specimen is then transferred to a round-bottomed flask containing 3 ml of a 0.375 molar solution of one of the monomers 1-4 in absolute acetone. After 24 h of reaction at 40° C. (absence of oxygen and moisture) the reaction is halted by addition of 5 drops of ethyl vinyl ether, and the specimens are removed, washed repeatedly with acetone, and dried at 80° C.

Characterization of Graft Copolymers 1, 2, 3, and 4

Characteristic FTIR Bands:

Graft copolymer 1 (obtained from monomer 1): 1729 cm$^{-1}$

Graft copolymer 2 (obtained from monomer 2): 1731 cm$^{-1}$

Graft copolymer 3 (obtained from monomer 3): 1729 cm$^{-1}$

Graft copolymer 4 (obtained from monomer 4): 1732 cm$^{-1}$

Example 4

Preparation of a Compound of Polyethylene and Polymer 3

0.2 g of polymer 3 was processed to mixtures with 3.8 g of polyethylene (HDPE; high density polyethylene) using a laboratory compounder (HAAKE Minilab Micro-Compounder). Compounding took place in two stages (stage 1 and stage 2), after which a strand was extruded. The processing conditions can be seen from Table 1.

TABLE 1

|  | Stage 1 | Stage 2 | Strand extrusion |
| --- | --- | --- | --- |
| Time [min] | 2 | 1 | 1.5 |
| Speed [rpm] | 45 | 35 | 55 |
| Melt temperature [° C.] | 190 | 190 | 190 |

The resulting polymer strand was shaped into test plates measuring 40×40×1 mm, using a Collin P 200 PV vacuum plate press. The temperature program of polymer shaping can be seen from Table 2.

TABLE 2

| | Temperature [° C.] | | | | |
| --- | --- | --- | --- | --- | --- |
| | 170 | 170 | 170 | 170 | 40 |
| Time [min] | 2 | 2 | 5 | 5 | 15 |
| Pressure [bar] | 2 | 10 | 50 | 100 | 100 |

Example 5

Characterization of the Surfaces of Polymers 1, 2, 3, 4 and of Graft Copolymers 1, 2, 3, 4

The glass transition temperatures (Tg) of polymers 1, 2, 3 and 4 were determined using a Pyris Diamond DSC (Perkin Elmer) DSC calorimeter (5 mg sample in each case; 2 heating runs from −50° C. to +150° C.; heating rate of 20° C./min; cooling rate 10° C./min). The glass transition temperatures (Tg) were determined in the 1st cooling run and in the 2nd heating run; the value reported in each case is the midpoint figure (see Table 3).

The thermal stability of the polymers was tested using a thermogravimetry unit (STA 625 from Rheometrics Ltd.) (5 mg sample in each case; nitrogen atmosphere with 35 ml/min nitrogen flow rate; heating rate 10° C./min; samples heated from room temperature to 500° C.). The onset of thermal degradation of the polymers was determined from the change in weight with temperature, and was reported in ° C. (see Table 3).

TABLE 3

| Polymer | $T_g$ [° C.] 1st cooling run | $T_g$ [° C.] 2nd cooling run | Decomposition temperature [° C.] |
| --- | --- | --- | --- |
| 1 | 31 | 33 | 211 |
| 2 | 33 | 33 | 358 |
| 3 | 6 | 8 | 221 |
| 4 | −19 | −16 | 223 |

Films of the polymers 1, 2, 3, and 4 were produced on glass surfaces by rotation coating from chloroform solution. The contact angle (test liquids: water and α-bromonaphthalene) was determined by the sessile drop method using a drop shape analysis system DSA100 (Krüss) (testing at 20-25° C.; drop volume: ~20 µl; reading after 1 s). The contact angle data were used to calculate the surface energies ($\gamma s$, $\gamma s^d$ and $\gamma s^P$, in mJ/m²) by the method of Owens and Wendt (J. Appl. Polymer Sci., 1969, 13, 1741 ff.).

The isoelectric point of the polymers (in the form of films on glass plates) was determined by means of measurements of streaming potential (Anton Paar electrokinetic analyzer EKA; clamping cell with PMMA counterplate; 0.001 molar KCl electrolyte solution); the data were evaluated by the method of Fairbrother and Mastin (J. Chem. Soc. 1924, 75, 2318 ff.) (see Table 4).

TABLE 4

| Polymer | Iso-electric point [pH] | Contact angle [°] H₂O | Contact angle [°] α-bromo-naphthalene | $\gamma s$ [mJ/m²] | $\gamma s^d$ [mJ/m²] | $\gamma s^P$ [mJ/m²] |
|---|---|---|---|---|---|---|
| 1 | 7.50 | 78 | 38.3 | 40.63 | 35.50 | 5.13 |
| 2 | 6.79 | 4.3 | 51.9 | 30.53 | 29.13 | 1.40 |
| 3 | 7.76 | 89.2 | 37.2 | 37.53 | 35.97 | 1.56 |
| 4 | 7.62 | 74.4 | 50.5 | 38.25 | 29.84 | 8.41 |

Graft copolymers 1, 2, 3, and 4 possess the following surface properties, determined as described above and compared with cleaned EPDM surfaces (see Table 5):

TABLE 5

| Polymer | Contact angle [°] H₂O | Contact angle [°] α-bromo-naphthalene | $\gamma s$ [mJ/m²] | $\gamma s^d$ [mJ/m²] | $\gamma s^P$ [mJ/m²] |
|---|---|---|---|---|---|
| EPDM | 108.3 | 60.4 | 24.96 | 24.91 | 0.05 |
| Graft copolymer 1 | 83.5 | 24.3 | 42.98 | 40.73 | 2.25 |
| Graft copolymer 2 | 96.5 | 43.3 | 33.84 | 33.28 | 0.56 |
| Graft copolymer 3 | 88.4 | 49.2 | 33.14 | 30.48 | 2.66 |
| Graft copolymer 4 | 98.8 | 55.1 | 28.37 | 27.58 | 0.79 |

Example 6

Determination of the Antimicrobial Activity of Polymers 1, 2, 3, 4, of Graft Polymer 3, and of the Compound of Polyethylene and Polymer 3

Determination of the Antimicrobial Activity of Polymers 1, 2, 3, 4

For the microbiological testing, 1% strength solutions of polymers 1, 2, 3, and 4 in chloroform were prepared. From these solutions, polymer films were applied to glass plaques measuring 40×40 mm (rotational coating). On these plaques the antimicrobial activity of polymers 1, 2, 3, and 4 was tested in accordance with Japanese industry standard JIS Z 2801: 2000, using the test organisms *Staphylococcus aureus* (DSM 346) and *Escherichia coli* (DSM 787). As samples for comparison, plaques of LLDPE (Dowlex 2388; linear low density polyethylene (containing 1-octene)) were tested.

The living microbe counts CFU/ml (colony-forming units per milliliter) were determined directly after inoculation (start) and after 24 hours of incubation for the polymers 1, 2, 3, and 4 and for the LLDPE comparison sample (see Table 6).

TABLE 6

| | *Staphylococcus aureus* | *Escherichia coli* |
|---|---|---|
| Start [CFU/ml] | $1.1 \cdot 10^5$ | $1.15 \cdot 10^5$ |
| LLDPE comparison sample [CFU/ml] | $8.9 \cdot 10^6$ | $8.5 \cdot 10^6$ |
| Polymer 1 [CFU/ml] | 0 | 0 |
| Polymer 2 [CFU/ml] | 50 | 0 |
| Polymer 3 [CFU/ml] | 0 | 0 |
| Polymer 4 [CFU/ml] | 0 | 2000 |

Determination of the Antimicrobial Activity of Graft Copolymer 3

For the microbiological testing of graft copolymer 3, a 40×40 mm glass plaque was coated with EPDM rubber (Dutral TER 4049; EPDM terpolymer of 55% ethylene, 40% propylene, and 5% ethylidenenorbornene). The EPDM film was crosslinked by UV radiation with 2-hydroxy-2-methyl-1-phenyl-1-propanone (photoinitiator from Ciba), as described in Example 6. This specimen was placed in 80 ml of a 0.0015 solution of the catalyst "Bispyridine Complex 6" in absolute acetone, and the tightly sealed reaction batch was heated at 40° C. for 2 h under an inert gas atmosphere. After that time the specimen was removed and washed with acetone to remove unattached initiator, under a nitrogen atmosphere. The specimen treated in this way was transferred to a laboratory autoclave containing 80 ml of a 0.375 molar solution of monomer 3 in absolute acetone. The sealed reaction vessel was heated at 40° C. for 24 h (absence of oxygen and moisture). Then the reaction was halted by addition of about 1 ml of ethyl vinyl ether, and the specimen was removed, washed repeatedly with acetone to remove residual monomer and homopolymer, and dried at 80° C. The product was characterized by means of NMR, FTIR, UV.

On the specimens thus treated the antimicrobial activity of graft copolymer 3 was tested in accordance with Japanese industry standard JIS Z 2801:2000, using the test organisms *Staphylococcus aureus* (DSM 346) and *Escherichia coli* (DSM 787). As samples for comparison, plaques of LLDPE (Dowlex 2388; linear low density polyethylene (containing 1-octene)) were tested.

The living microbe counts CFU/ml (colony-forming units per milliliter) were determined directly after inoculation (start) and after 24 hours of incubation for the graft copolymer 3 and for the LLDPE comparison sample (see Table 7).

TABLE 7

| | *Staphylococcus aureus* | *Escherichia coli* |
|---|---|---|
| Start [CFU/ml] | $3.5 \cdot 10^5$ | $3.9 \cdot 10^5$ |
| LLDPE comparison sample [CFU/ml] | $5.64 \cdot 10^6$ | $7.56 \cdot 10^6$ |
| Graft copolymer 3 [CFU/ml] | $4.20 \cdot 10^4$ | $5.10 \cdot 10^4$ |

Determination of the Antimicrobial Activity of the Compound of Polyethylene and Polymer 3

The test plates produced as per Example 4, containing 5 percent by weight of polymer 3 in HDPE, were tested for antimicrobial activity in accordance with Japanese industry standard JIS Z 2801:2000 in respect of the bacteria *Staphy-* lococcus aureus (DSM 346) and Escherichia coli (DSM 787). As a comparison sample, plates of pure HDPE were tested.

The living microbe counts CFU/ml (colony-forming units per milliliter) were determined directly after inoculation (start) and after 24 hours of incubation for the HDPE/polymer 3 compound and for the comparison sample (pure HDPE) (see Table 8).

TABLE 8

|  | Staphylococcus aureus | Escherichia coli |
|---|---|---|
| Start [CFU/ml] | $3.5 \cdot 10^5$ | $3.9 \cdot 10^5$ |
| HDPE comparison sample [CFU/ml] | $5.64 \cdot 10^6$ | $7.56 \cdot 10^6$ |
| Compound [CFU/ml] | $3.00 \cdot 10^4$ | $3.78 \cdot 10^4$ |

Example 7

Preparation of Monomer 5

4-(exo,endo-Bicyclo[2.2.1]hept-5-en-2-yl)benzyl 2-dimethyl-amino)ethyl ether 100 mmol of 4-vinylbenzyl chloride (from Fluka), 200 mmol of freshly cracked cyclopentadiene (bp=41° C.), and 10 mmol of BHT (2,6-di-tert-butyl-4-methylphenol; stabilizer) are mixed with stirring in a reaction flask equipped with a top-mounted condenser (reflux condenser), and the mixture is heated under reflux. Heating is carried out using an oil bath with a temperature of 185° C. The reaction time is 12 hours. After cooling, the crude reaction product is distilled under reduced pressure (<1 mbar). At a boiling temperature in the range 90 to 100° C., the product is obtained as a virtually colorless liquid. The product obtained by distillation is purified further by column chromatography (silica gel as stationary phase; eluent:cyclohexane/ethyl acetate in a volume ratio of 50/1). This gives the purified intermediate 4-(exo,endo-bicyclo[2.2.1]hept-5-en-2-yl)benzyl chloride (also referred to as 5-(4-chloromethylphenyl)bicyclo[2.2.1]-hept-2-ene) in a yield of 11 mmol (11% of theory). Analytical data for 4-(exo,endo-bicyclo[2.2.1]hept-5-en-2-yl)benzyl chloride:

NMR (1H, 500 MHz, CDCl$_3$): 7.27, 7.25, 7.15, 7.14 (aromatic C—H), 6.27, 5.80 (CH=CH in the ring), 4.59, 4.57 (phenyl-CH$_2$—Cl).

FTIR (film on CaF$_2$, cm$^{-1}$): 1265 (benzyl chloride group), 1614, 1513 (aromatic), 3057 (=CH— in the ring)

In the next reaction step the procedure is as follows: 4.5 mmol of 2-dimethylaminoethanol are dissolved under an inert gas atmosphere in 10 milliliters of absolute (anhydrous) dimethylformamide. Then at room temperature 7.2 mmol of sodium hydride (in the form of a 60% dispersion in mineral oil) are added with stirring. After 30 min 5 mmol of the intermediate 4-(exo,endo-bicyclo[2.2.1]hept-5-en-2-yl)benzyl chloride, in solution in 10 milliliters of dimethylformamide, are added dropwise over a period of 10 min under an inert gas atmosphere. Subsequently the reaction mixture is heated at 60° C. for 12 hours with stirring. After the end of the reaction, 50 milliliters of water are added, and then 2 g of sodium hydrogen carbonate (in powder form) are added. This mixture is extracted with 100 milliliters of dichloromethane. The dichloromethane extract is washed with aqueous sodium hydrogen carbonate solution (2 g in 50 milliliters of water) and then dried over sodium sulfate. The solvent is then stripped off under reduced pressure at a temperature of 80° C. The residue which remains is taken up in 20 milliliters of n-heptane and freed from insolubles by filtration. Gaseous hydrogen chloride is introduced into the heptane solution, leading to the formation of a white precipitate. This precipitate represents the hydrochloride of 4-(exo,endo-bicyclo [2.2.1]hept-5-en-2-yl)benzyl 2-(dimethyl-amino)ethyl ether. This precipitate is separated off by filtration, washed with 20 milliliters of n-heptane, and dried under reduced pressure at 40° C. The dried product is introduced into a solution of 2 g of sodium hydrogen carbonate in 50 milliliters of water and is extracted with 100 milliliters of dichloromethane. The dichloromethane extract is washed with aqueous sodium hydrogen carbonate solution (2 g in 50 milliliters of water) and then dried over sodium sulfate. The solvent is then stripped off under reduced pressure at a temperature of 40° C. This gives 3.8 mmol of 4-(exo,endo-bicyclo[2.2.1]hept-5-en-2-yl)benzyl 2-(dimethylamino)ethyl ether, also referred to as [2-(4-{bicyclo[2.2.1]hept-5-en-2-yl}benzyloxy)ethyl]dimethylamine, in the form of a pale yellow liquid. This corresponds to a yield of 76% (based on 4-(exo,endo-bicyclo [2.2.1]hept-5-en-2-yl)benzyl chloride).

Analytical data for 4-(exo,endo-bicyclo[2.2.1]hept-5-en-2-yl)benzyl 2-(dimethylamino)ethyl ether:

NMR (1H, 500 MHz, CDCl$_3$): 7.10-7.26 (aromatic C—H), 6.25, 5.78 (CH=CH in the ring), 4.51, 4.48 (phenyl-CH$_2$—O—); 3.53 (—O—CH$_2$—CH$_2$—N), 2.52 (—O—CH$_2$—CH$_2$—N), 2.26, 2.27 (N—CH$_3$).

FITR (film on CaF2, cm$^{-1}$): 1615, 1514 (aromatic), 1106 (benzyl ether C—O—C), 2768 (N—CH$_2$—), 3057 (=CH— in the ring)

Example 8

Preparation of Polymer 5 by Means of ROMP

Poly{4-(bicyclo[2.2.1]hept-5-en-2-yl)benzyl 2-(dimethyl-amino)ethyl ether}

0.37 mmol of 4-(exo,endo-bicyclo[2.2.1]hept-5-en-2-yl) benzyl 2-(dimethylamino)ethyl ether is dissolved under an inert gas atmosphere in 5 milliliters of absolute (anhydrous) dichloromethane which has been freed from dissolved oxygen. Then 0.0012 mmol of "Bispyridine Complex 6" catalyst (Love et al., *Angew. Chem.*, 2002, 114(21), 4207-4209), in solution in 3 ml of absolute dichloromethane, is added with stirring. The reaction mixture is stirred at room temperature for 24 h in the absence of moisture and oxygen. Then the reaction is terminated by addition of 5 drops of ethyl vinyl ether. The reaction solution is concentrated under reduced pressure. The resulting polymer is precipitated from n-pentane, then reprecipitated from dichloromethane/n-pentane and dried to constant weight under reduced pressure at 40° C.

This gives 81 mg of poly{4-(bicyclo[2.2.1]hept-5-en-2-yl) benzyl 2-(dimethylamino)ethyl ether}, also referred to as poly{[2-(4-{bicyclo[2.2.1]hept-5-en-2-yl}benzyloxy) ethyl]-dimethylamine}, in the form of a pale yellow solid. The polymer is soluble, for example, in the following solvents: dichloromethane, chloroform.

Analytical data for polymer 5:

NMR (1H, 500 MHz, CDCl$_3$): 4.8-5.7 (CH=CH in the main chain), 7.18 (aromatic), 4.48 (phenyl-CH$_2$—O), 3.54 (—O—CH$_2$—CH$_2$—N), 2.54 (—O—CH$_2$—CH$_2$—N), 2.27 (N—CH$_3$).

FTIR (polymer film on CaF$_2$, cm$^{-1}$): 2768 (N—CH$_2$—), 1615, 1514 (aromatic), 1105 (benzyl ether C—O—C), 966 (=CH— in the main chain)

Example 9

Determination of the Antimicrobial Activity of Polymer 5

For the microbiological testing a 1% strength solution of polymer 5 in chloroform was prepared. From these solutions, polymer films were applied to glass plaques measuring 40×40 mm (rotational coating). These plaques were used to test the antimicrobial activity of polymer 5 in accordance with Japanese industry standard JIS Z 2801:2000, using the test microbes *Staphylococcus aureus* (DSM 346). As comparison samples, uncoated glass plaques were tested.

The living microbe counts CFU/ml (colony-forming units per milliliter) were determined directly after inoculation (start) and after 24 hours of incubation for polymer 5 and the comparison sample (glass) (see Table 9).

TABLE 9

|  | *Staphylococcus aureus* |
|---|---|
| Start [CFU/ml] | $6.00 \cdot 10^5$ |
| Comparison sample (glass) [CFU/ml] | $9.77 * 10^5$ |
| Polymer 5 [CFU/ml] | $1.86 * 10^3$ |

What is claimed is:

1. Biocidal polymers comprising structural repeating units according to formula 1

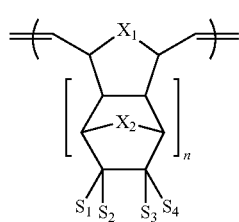

formula 1 n = 0, 1 where X1 and X2 are selected from the group consisting of —CH$_2$—, —CH$_2$—CH$_2$—, —O— and =(C=C(R1)R2),
wherein R1 and R2=H, or straight-chain or branched $C_1$-$C_{20}$ alkyl
where S1, S2, S3 and S4=H, or straight-chain or branched $C_1$-$C_{20}$ alkyl, or cycloalkyl, or aralkyl, or alkylaryl, where at least one of the substituents S1, S2, S3 and S4 has a structure a-d, or -a-b-d, or -b-c-d, or -a-b-c-d,
and where a is a straight-chain or branched $C_2$-$C_{20}$ alkylene, or a siloxane, or an oligo- or poly-siloxane having 1-20 repeating units, or a $C_2$-$C_4$ alkylene glycol or $C_2$-$C_4$ polyalkylene glycol having 1-20 repeating units, or cyclohexylene, or cycloheptylene, or naphthylene,
and where b is —O—, or —O—CO—, or —CO—O—, or —O—OC—O—, or —CO—, or —CO—NH—, or —NH—CO—, or —N(R3)— where R3=H, straight-chain or branched $C_1$-$C_6$ alkyl, or phenyl, or benzyl, or phenylethyl, or nonylphenyl,
and where c is a straight-chain or branched $C_1$-$C_{20}$ alkylene, or a siloxane, or an oligo- or poly-siloxane having 1-20 repeating units, or a $C_2$-$C_4$ alkylene glycol or $C_2$-$C_4$ polyalkylene glycol having 1-20 repeating units, or cyclohexylene, or cycloheptylene, or naphthylene,
and where d is -e(R4)R5 where e=N or P, where the group -e(R4)R5 is a guanidinyl radical —NH—C(NH)—NH$_2$, or an N-substituted guanidinyl radical, or a biguanidinyl radical, or a hydrazinyl radical —NH—NH2 or an N-substituted hydrazinyl radical,
and where the radicals R4 and R5=H, or straight-chain or branched $C_1$-$C_{20}$ alkyl, or benzyl, or phenylethyl, or cyclopentyl, or cyclohexyl, or cycloheptyl, or furyl, or pyrrolyl, or pyridinyl,
or where the radicals R4 and R5 together with N of the group —N(R4)R5 form an aziridine, or pyrrole, or pyridine ring, where the nitrogen of the group —N(R4)R5 in such unsaturated rings optionally forms a double bond to one of the substituents R4, R5 and is therefore in quaternized form in the group —N(R4)R5, or together with N of the group —N(R4)R5 and with one or more further unsubstituted or substituted heteroatoms from the group —O—, or —S, or —NH—, or —N(R6)— where R6=H, or straight-chain or branched $C_1$-$C_{20}$ alkyl, or benzyl, or phenylethyl, or nonylphenyl, or cyclopentyl, or cyclohexyl, or cycloheptyl, form an oxazole, or triazole, or tetrazole, or triazine, or tetrazine, or thiomorpholine, or imidazole, or thiazole, or thiadiazole, or pyrimidine, or pyrazine, or pyridazine, or piperazine or N-substituted piperazine ring, where the nitrogen of the group —N(R4)R5 in such unsaturated rings may optionally form a double bond to one of the substituents R4, R5 and therefore is in quaternized form in the group —N(R4)R5,
or where d is a 5-8-membered saturated or unsaturated heterocycle comprising N and one or more further unsubstituted or substituted heteroatoms from the group —O—, —S—, —NH—, and —N(R6)— where R6=H, or straight-chain or branched $C_1$-$C_{20}$ alkyl, or benzyl, or phenylethyl, or nonylphenyl, or cyclopentyl, or cyclohexyl, or cycloheptyl, whose bond to the component a, b or c of the substituent S1, S2, S3 or S4 is via a ring carbon, and also cationic derivatives and saturated derivatives of these polymers.

2. The biocidal polymers of claim 1, where n is 0.

3. The biocidal polymer of claim 1, wherein the polymer is a homopolymer or a copolymer.

4. The biocidal polymer of claim 3, wherein the polymer is a copolymer and wherein the copolymer is a random copolymer, or an alternating copolymer, or a block copolymer or a graft copolymer.

5. A biocidal polymer blend comprising one or more biocidal polymers according to claim 1 and one or more further polymers.

6. The biocidal polymer blend of claim 5, wherein the further polymers are selected from the group consisting of polyurethanes, polyolefins, polyethylene, polypropylene, polysiloxane, polystyrene, polyacrylates, polymethyl methacrylate, PVC, polyamide and polyterephthalate.

7. The biocidal polymers of claim 1, wherein the ring carbon bonding the 5-8 membered saturated or unsaturated heterocycle to component a, b or c of the substituent S1, S2, S3 or S4 is selected from the group consisting of an oxazole, triazole, tetrazole, triazine, tetrazine, morpholine, thiomorpholine, imidazole, thiazole, thiadiazole, pyrimidine, pyrazine, pyridazine, piperzine and an N-substituted piperazine heterocycle.

* * * * *